(12) United States Patent
Zhou et al.

US010836767B2

(10) Patent No.: US 10,836,767 B2
(45) Date of Patent: Nov. 17, 2020

(54) SERUM STABLE PRO-COELENTERAZINE ANALOGUES

(71) Applicant: PROMEGA CORPORATION, Madison, WI (US)

(72) Inventors: Wenhui Zhou, San Luis Obispo, CA (US); Brock Binkowski, Sauk City, WI (US); Poncho Meisenheimer, San Luis Obispo, CA (US); Andrew L. Niles, Madison, WI (US); Kevin Kupcho, Madison, WI (US); James Unch, Arroyo Grande, CA (US)

(73) Assignee: PROMEGA CORPORATION, Madison, WI (US)

( * ) Notice: Subject to any disclaimer, the term of this patent is extended or adjusted under 35 U.S.C. 154(b) by 162 days.

(21) Appl. No.: 16/023,950

(22) Filed: Jun. 29, 2018

(65) Prior Publication Data

US 2019/0010157 A1     Jan. 10, 2019

Related U.S. Application Data

(60) Provisional application No. 62/529,152, filed on Jul. 6, 2017.

(51) Int. Cl.
| | | |
|---|---|---|
| *C07D 487/04* | (2006.01) | |
| *G01N 33/58* | (2006.01) | |
| *C12Q 1/66* | (2006.01) | |
| *G01N 21/76* | (2006.01) | |

(52) U.S. Cl.
CPC ............. *C07D 487/04* (2013.01); *C12Q 1/66* (2013.01); *G01N 33/582* (2013.01); *G01N 21/763* (2013.01); *G01N 2333/90241* (2013.01); *G01N 2333/916* (2013.01)

(58) Field of Classification Search
CPC ...... C07D 487/04; C12Q 1/66; G01N 21/763; G01N 2333/90241; G01N 2333/916; G01N 33/582
See application file for complete search history.

(56) References Cited

U.S. PATENT DOCUMENTS

| | | | | |
|---|---|---|---|---|
| 7,537,912 B2 * | 5/2009 | Wood | ................... | C07D 487/04 435/19 |
| 2009/0075309 A1 | 3/2009 | Gambhir | | |
| 2013/0005730 A1 * | 1/2013 | Sun | ....................... | C07D 263/04 514/236.8 |
| 2014/0221653 A1 * | 8/2014 | Blumberg | ............ | C07D 401/04 544/362 |

FOREIGN PATENT DOCUMENTS

| | | |
|---|---|---|
| WO | 2003040100 | 5/2003 |
| WO | 2012061530 | 5/2012 |

OTHER PUBLICATIONS

Kimura et al. J. Gene Medicine (2010) 12: 528-537 (Year: 2010).*
International Search Report for PCT/US2018/040440, dated Sep. 4, 2018, 5 pages.
Written Opinion of the International Searching Authority for PCT/US2018/040440, dated Sep. 4, 2018, 6 pages.
Levi et al. "Bisdeoxycoelenterazine Derivatives for Improvement of Bioluminescence Resonance Energy Transfer Assays" J. Am. Chem. Soc. 2007, 129, 11900-11901.

* cited by examiner

*Primary Examiner* — Susan M Hanley
(74) *Attorney, Agent, or Firm* — Casimir Jones, S.C.; Anne M. Reynolds

(57) ABSTRACT

Described are pro-coelenterazine analogues, methods for making the analogues, kits comprising the analogues, and methods of using the compounds for the detection of luminescence in luciferase-based assays or fragment complementary luciferase. The disclosed pro-coelenterazine analogues provide increased serum stability for live cell assays, and are capable of tuning the brightness and assay windows as needed for the applications.

31 Claims, 20 Drawing Sheets

SERUM STABLE PRO-COELENTERAZINE ANALOGUES

RELATED APPLICATIONS

This application claims the benefit of U.S. provisional application Ser. No. 62/529,152, filed Jul. 6, 2017, which is incorporated herein by reference in its entirety.

TECHNICAL FIELD

The present disclosure relates to pro-coelenterazine analogues, methods for making pro-coelenterazine analogues, and methods of using pro-coelenterazine analogues in luciferase-based live cell assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters or fragment complemented luciferases that enable whole-cell biosensor measurements, drug discovery through high-throughput screening, and in vivo imaging that also permit the study of protein-protein interactions in living cells, apoptosis, and cell viability. Luciferases that use coelenterazine and coelenterazine analogues as substrates are among the most widely used systems due to their brightness and acceptance in whole cell applications.

SUMMARY OF THE INVENTION

Many known coelenterazine analogues degrade rapidly in media or media with serum, which limits their effectiveness as luciferase substrates. Assay sensitivity and duration time are often limited by the background due to the instability of active coelenterazine or coelenterazine analogues. Pro-coelenterazine analogues, such as ester-protected coelenterazine or furimazine compounds, were introduced for live cell assays to improve assay performance by using esterases present in cells to remove the ester or carbonate group from the pro-coelenterazine analogue to release, over time, an active coelenterazine or furimazine substrate. However, among these pro-coelenterazine analogues, stability of the signal, which is needed for some live cell assays, over a certain duration time still remained a great challenge.

Short detection periods often limit practical applications for live cell assays, such as reporter gene assay, live-dead cell assays, cell apoptosis, protein-protein interactions, bacteria, fungi, or mold detections, or detection of activity of any target enzyme of interest in vitro or in cells. Accordingly, there exists a need for pro-coelenterazine analogues with improved stability, while maintaining reasonable brightness needed for live cell assays.

In one aspect, disclosed are compounds of formula (I),

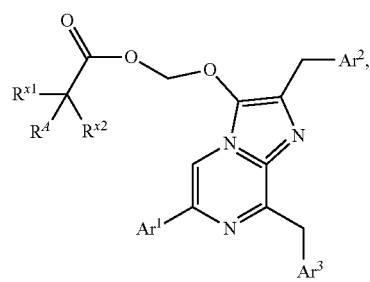

(I)

or a tautomer, or a salt thereof, wherein $Ar^1$, $Ar^2$, and $Ar^3$ are each independently selected from the group consisting of aryl and heteroaryl, wherein $Ar^1$, $Ar^2$, and $Ar^3$ are each optionally substituted; $R^4$ is selected from the group consisting of $C_2$-$C_{10}$ linear or branched alkyl, alkoxy, alkoxyalkyl, amido, acetoxy, methyl ether polyethylene glycoxy, methyl ether polyethylene glycoxyalkyl, haloalkyl, haloalkoxy, aryl, arylalkyl, cycloalkyl, hydroxyl alkyl, hydroxyl polyethylene glycoxyl, carboxyalkyl, heteroaryl, heteroarylalkyl, heterocycle, and heterocylic alkyl; $R^{x1}$, $R^{x2}$, at each occurrence, are each independently selected from the group consisting of $C_1$-$C_6$ linear or branched alkyl, optionally substituted by one or more substituents selected from the group consisting of alkoxy, aryl, cycloalkyl, heteroaryl, and heterocycle.

In the other aspect, disclosed are compounds of formula (II),

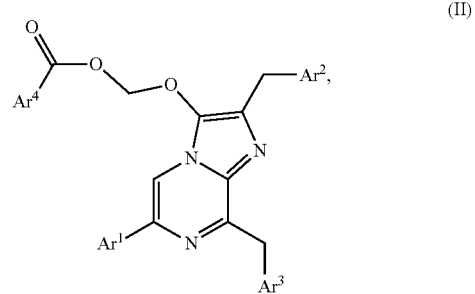

(II)

or a tautomer, or a salt thereof, wherein, $Ar^1$, $Ar^2$, and $Ar^3$ are each independently selected from the group consisting of aryl and heteroaryl, wherein $Ar^1$, $Ar^2$, and $Ar^3$ are each optionally substituted; $Ar^4$ is aryl, furan or thiophene, optionally substituted by one or more substituents selected from the group consisting of alkyl, alkoxy, aryl, cycloalkyl, heteroaryl, and heterocycle.

Disclosed are also compounds of formula (III),

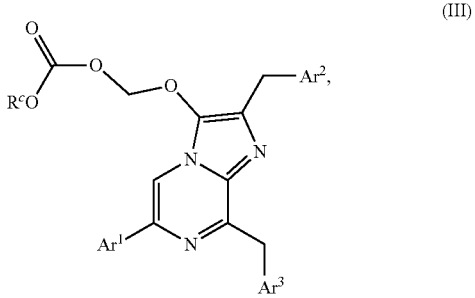

(III)

Wherein, $Ar^1$, $Ar^2$, and $Ar^3$ are each independently selected from the group consisting of aryl and heteroaryl, wherein $Ar^1$, $Ar^2$, and $Ar^3$ are each optionally substituted; $R^C$ is selected from the group consisting of $C_1$-$C_9$ linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocylic alkyl.

Also disclosed are methods of making the compounds, kits comprising the compounds, and methods of using the compounds as luciferase substrates in luciferase-based assays.

DETAILED DESCRIPTION

Figure 1A:
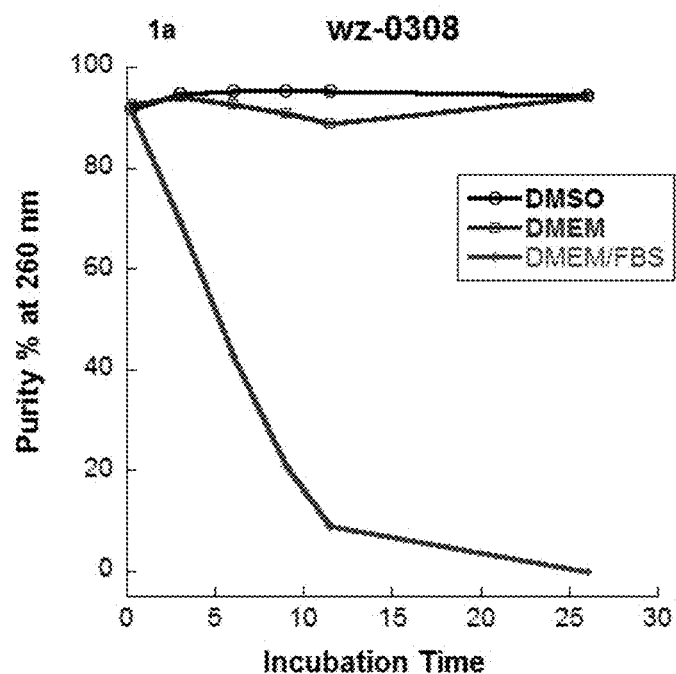
FIGS. 1A-1H show the changes of purity over time for serum instable compounds WZ-0308 (FIG. 1A), WZ-0310 (FIG. 1B), WZ-0315 (FIG. 1C), WZ-0415 (FIG. 1D), WZ-0429 (FIG. 1E), WZ-0439 (FIG. 1F), WZ-0454 (FIG. 1G), and WZ-0441 (FIG. 1H) at 40 μM in (1) DMSO, (2) DMEM media, or (3) DMEM/FBS (10%).
Figure 1B:
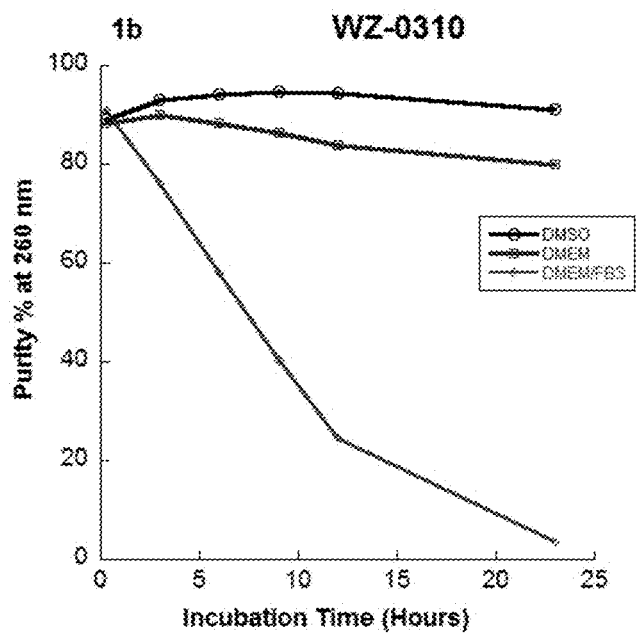
Figure 1C:
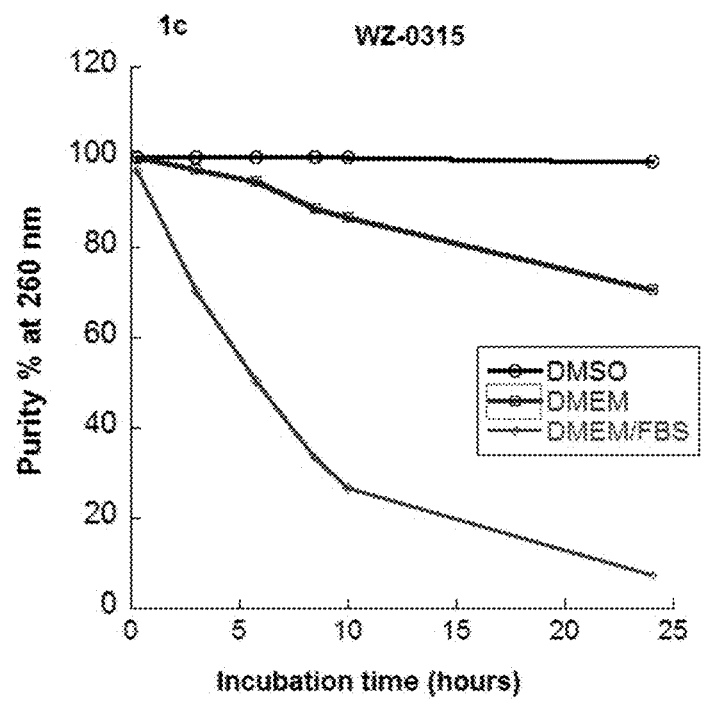
Figure 1D:
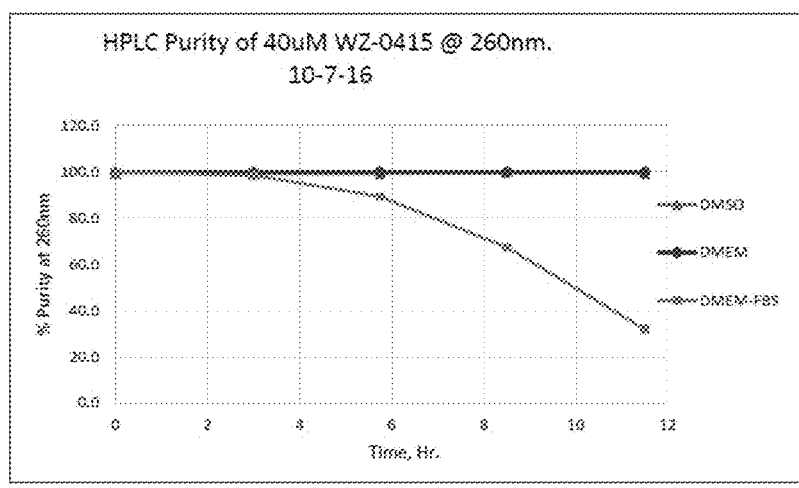
Figure 1E:
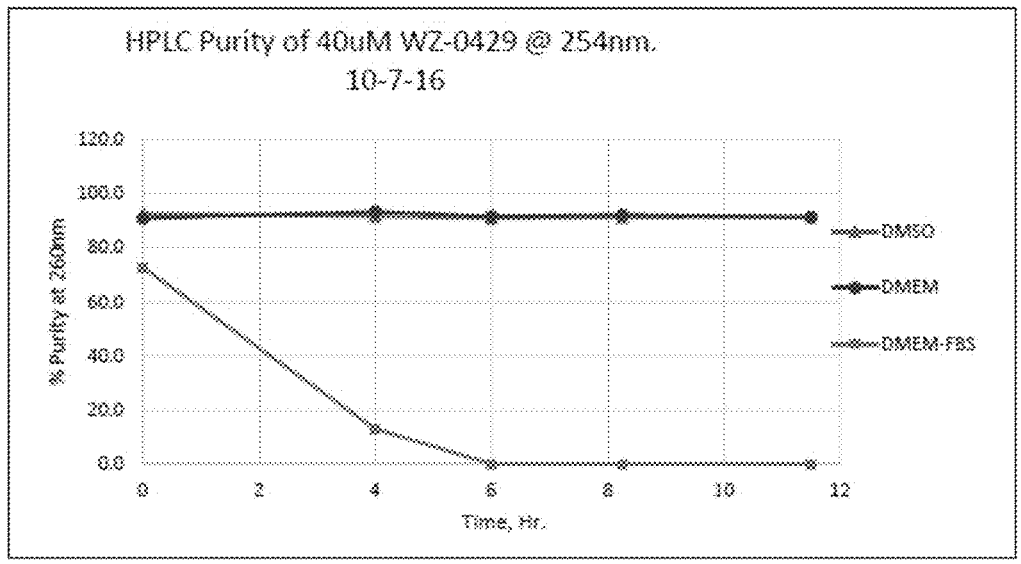
Figure 1F:
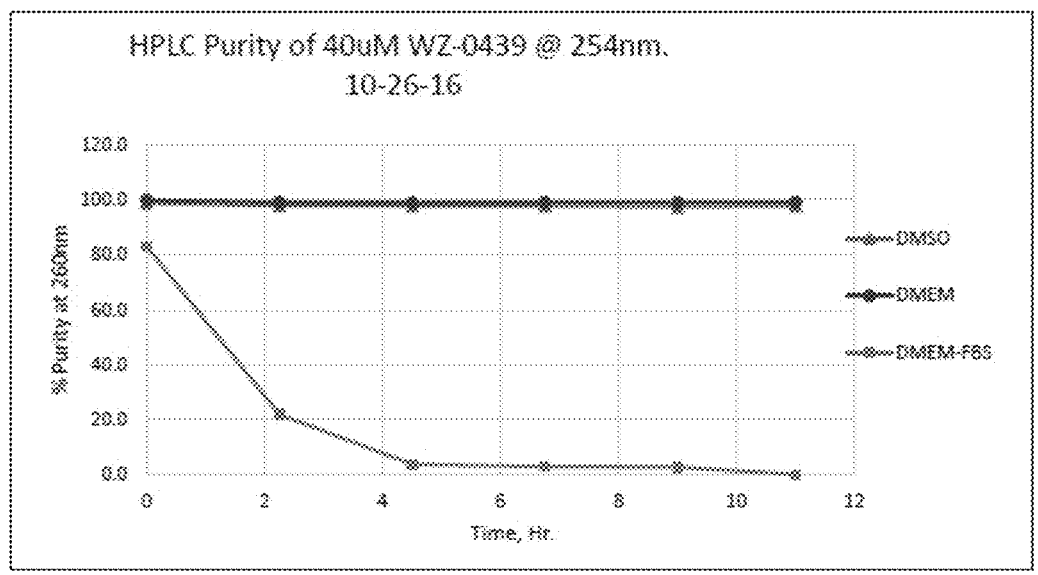
Figure 1G:
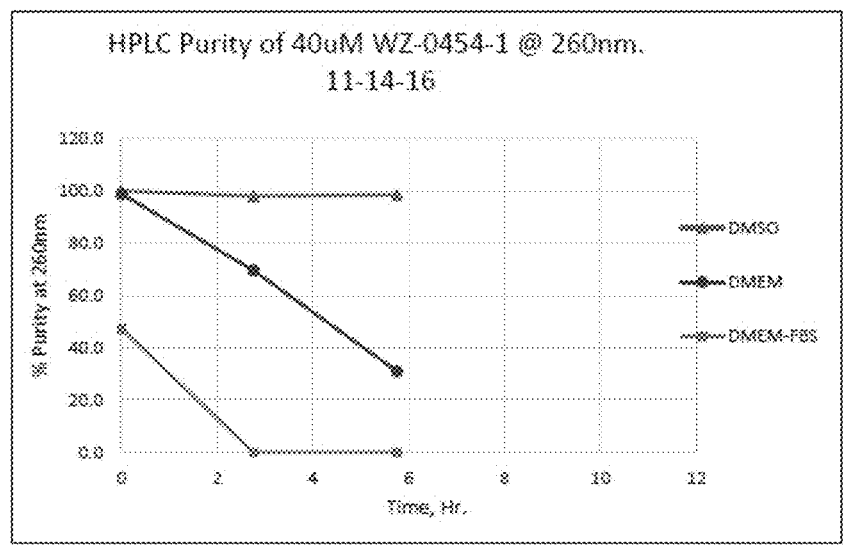
Figure 1H:
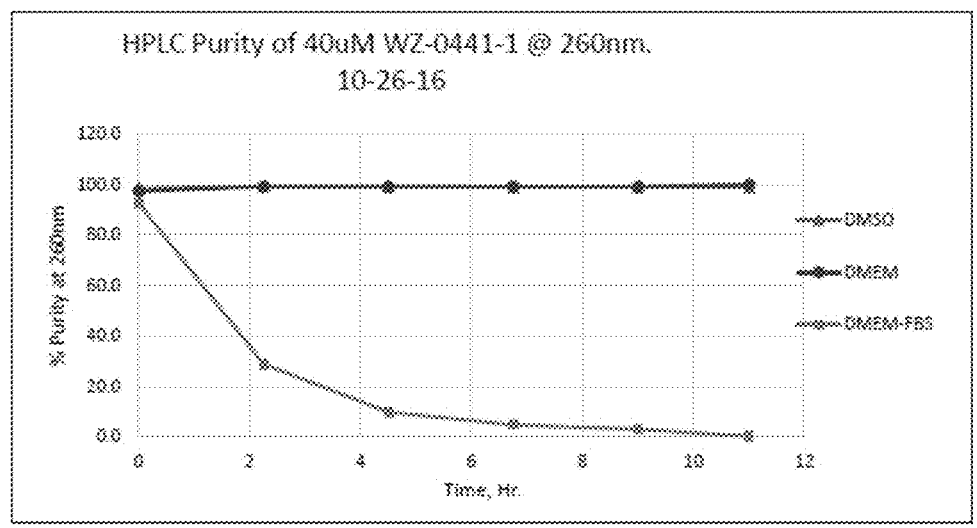
Figure 2A:
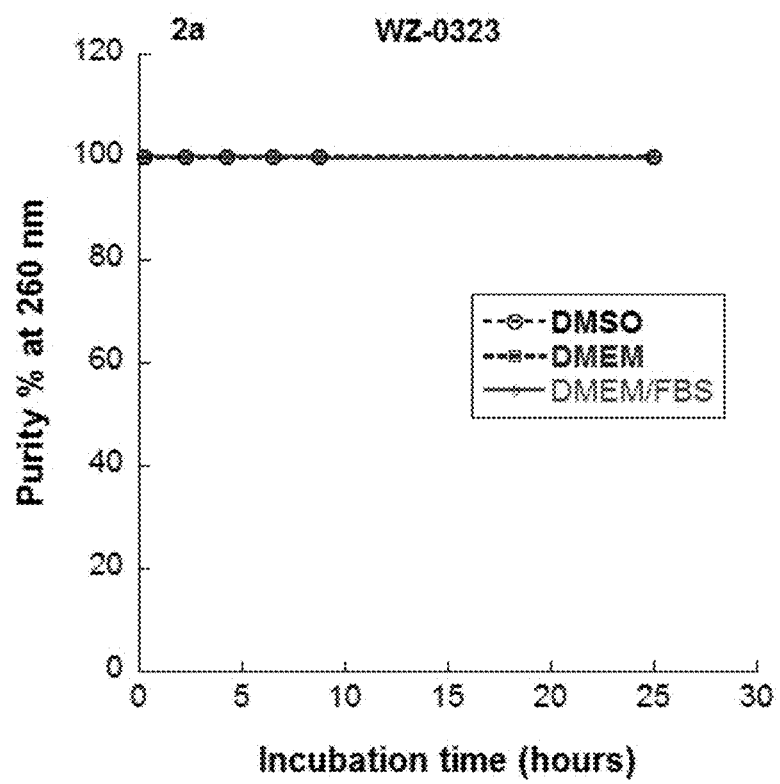
FIGS. 2A-2I show the changes of purity over time for the disclosed serum stable compounds WZ-0323 (FIG. 2A), WZ-0324 (FIG. 2B) and WZ-0336 (FIG. 2C), WZ-0451 (FIG. 2D), WZ-0467 (FIG. 2E), WZ-0420 (FIG. 2F), WZ-0461 (FIG. 2G), WZ-0416 (FIG. 2H) and WZ-0419 (FIG. 2I) at 40 μM in (1) DMSO, (2) DMEM media, or (3) DMEM/FBS (10%).
Figure 2B:
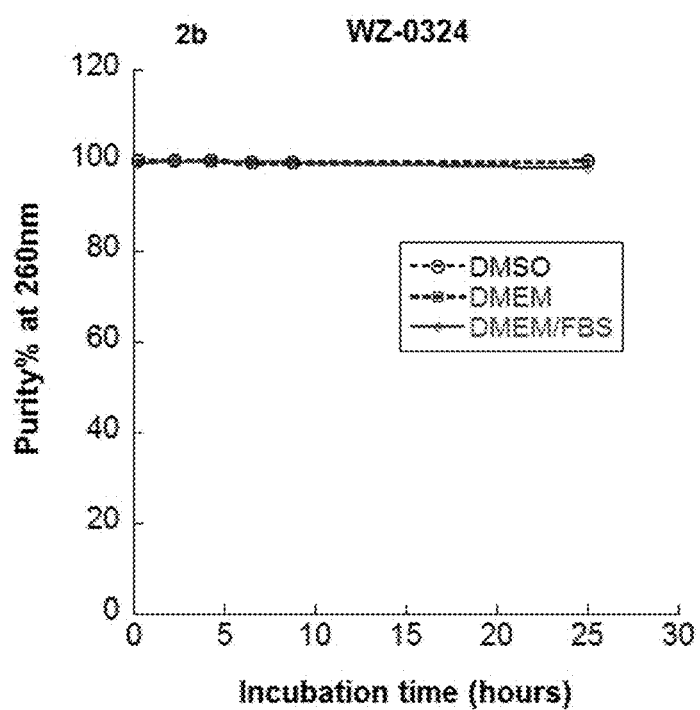
Figure 2C:
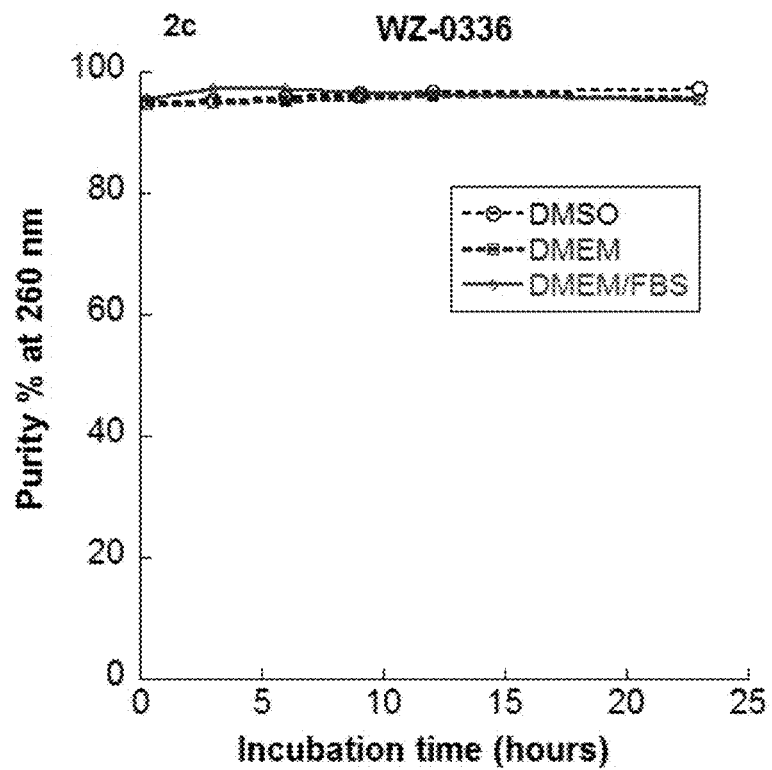
Figure 2D:
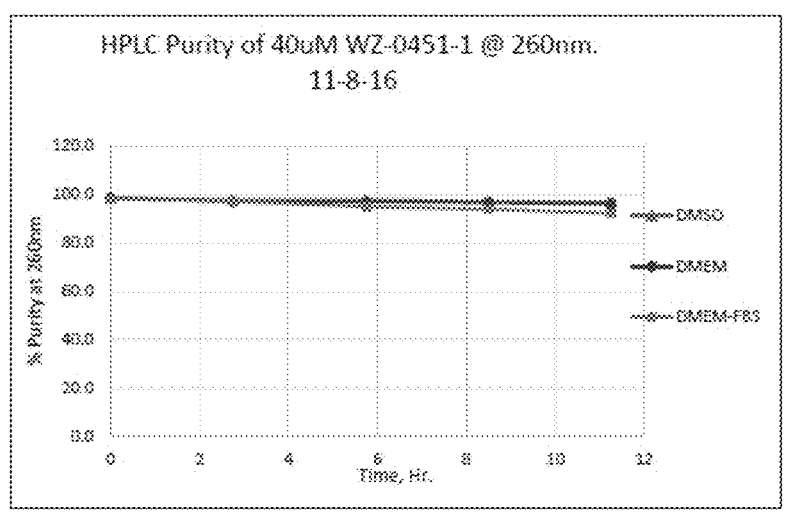
Figure 2E:
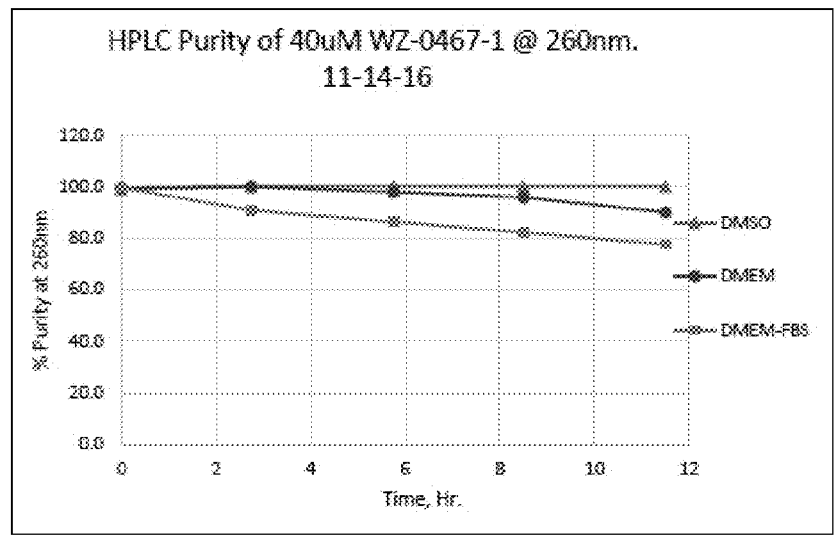
Figure 2F:
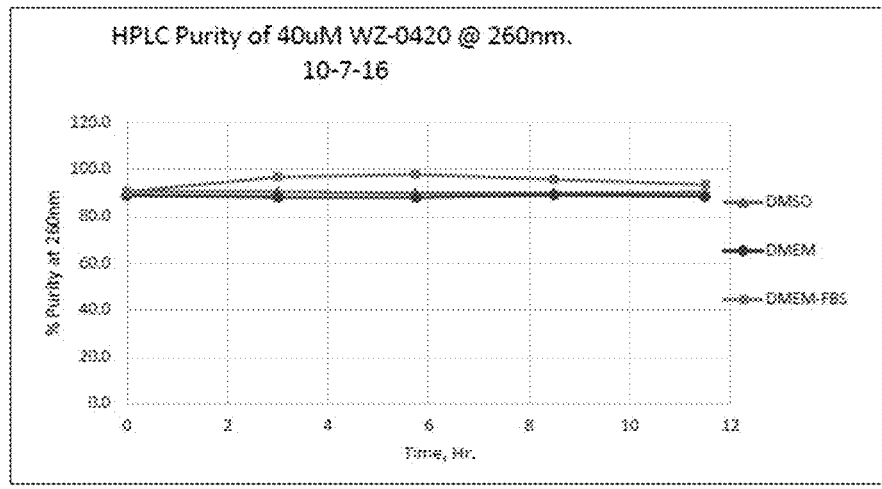
Figure 2G:
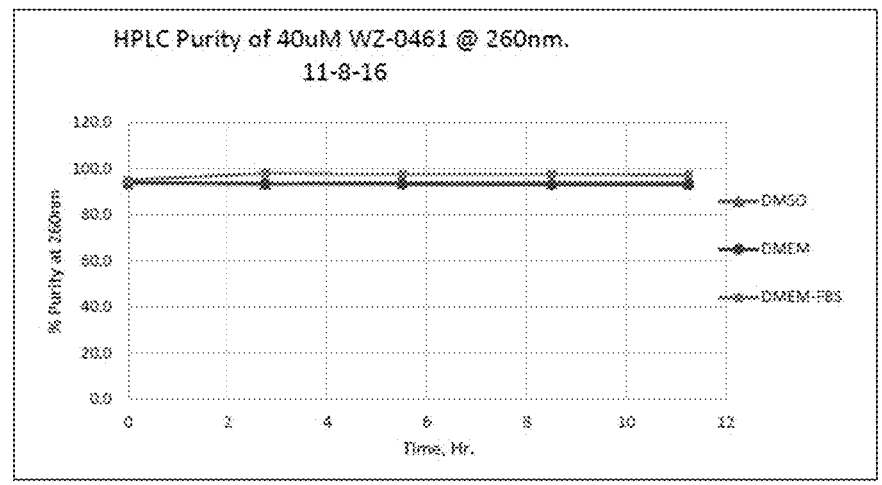
Figure 2H:
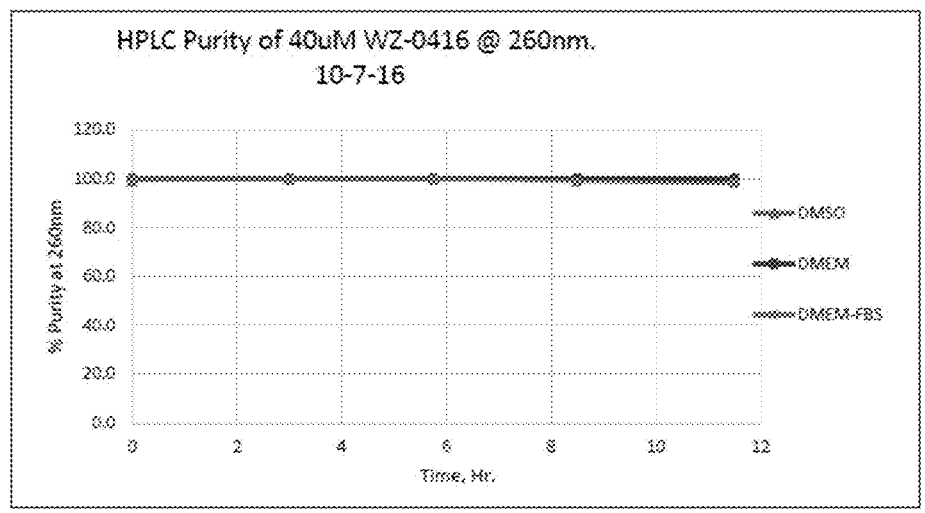
Figure 2I:
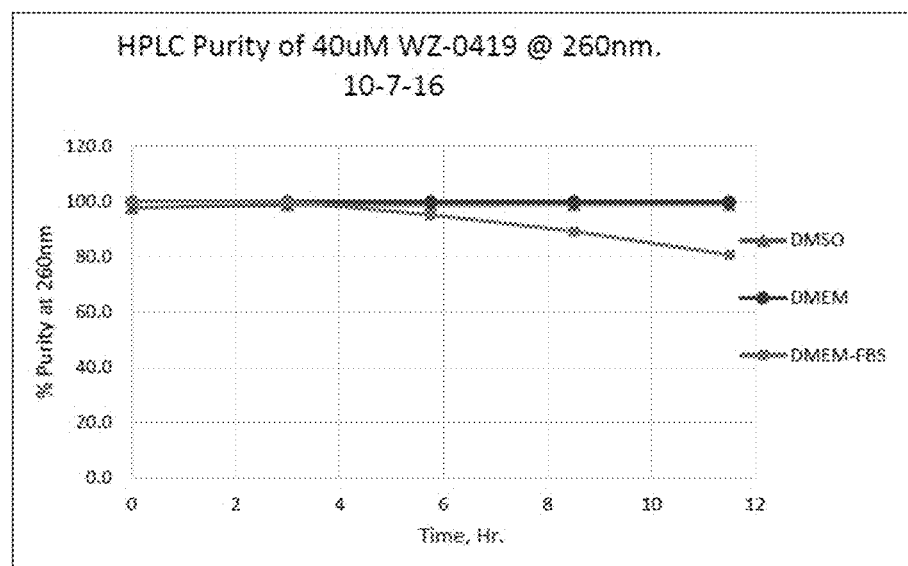

Disclosed herein are ester or carbonate derivatives of pro-coelenterazine analogues. These compounds may be substrates for a non-luminescent enzyme and pro-substrates for a luminescent protein. Once acted on by the non-luminescent enzyme of interest, the derivative can become a substrate for a luminescent protein. The disclosed compounds can be useful pro-substrates for proteins that utilize coelenterazine ("coelenterazine-utilizing enzymes") to produce luminescence, including, but not limited to, luciferases and photoproteins found in various marine organisms such as cnidarians (e.g., *Renilla* luciferase), jellyfish (e.g., aequorin from the *Aequorea* jellyfish), and decapods luciferases (e.g., luciferase complex of *Oplophorus gracilirostris*).

The disclosed compounds can exhibit unexpected stability in serum. The disclosed serum stable compounds can provide a luminescent signal for a duration time up to 24 hours in many live cell bioluminescent assays, live cell imaging, or bioluminescence cell sorting methods. The disclosed compounds provide great potential by enabling new assays due to the significant improvement in serum stability. This unexpected benefit provides great potential for future improvements with bioluminescent assay performance by fine tuning serum liability and/or related esterase activity by improving the brightness, solubility, and/or cell permeability as needed.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acetoxy" as used herein, means alchol when attached via carbonyl group.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. The alkenyl group may be substituted or unsubstituted. For example, the alkenyl group may be substituted with an aryl group, such as a phenyl.

The term "alkynyl" as used herein, means a hydrocarbon chain containing from 2 to 10 carbon atoms with at least one carbon-carbon triple bond. The alkynyl group may be substituted or unsubstituted. For example, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms.

Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "amido" as used herin, means —NH— when attached via a carbonyl group, such as CH$_3$C(O)NH— or CH$_3$CH$_2$CONH—.

The term "amino acid" refers to both natural and unnatural amino acids. It also includes protected natural and unnatural amino acids.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "arylalkyl" as used herein, refers to an aryl group, as defined herein, appended to the parent molecule moiety through an alkyl group, as defined herein. In some embodiments, the alkyl group may be $C_1$-$C_6$ alkyl.

Ther term "carbonate" as used herein, means —OC(O)O—.

The term "carboxyalkyl" as used herein, refers to a carboxy group (—COOH), appended to the parent molecule moiety through an alkyl group, as defined herein. In some embodiments, the alkyl group may be $C_1$-$C_6$ alkyl.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "carboxyalkyl" as used herein, refers to a carboxy group, as defined herein, appended to the parent molecule moiety through an alkyl group, as defined herein. In some embodiments, the alkyl group may be $C_1$-$C_6$ alkyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine.

Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms have been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heteroarylalkyl" as used herein, refers to a heteraryl group, as defined herein, appended to the parent molecule moiety through an alkyl group, as defined herein. In some embodiments, the alkyl group may be $C_1$-$C_6$ alkyl.

The term "heterocycle" or "heterocyclic", as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heterocyclic alkyl" as used herein, refers to a heterocycle, as defined herein, appended to the parent molecule moiety through an alkyl group, as defined herein. In some embodiments, the alkyl group may be $C_1$-$C_6$ alkyl.

The term "hydroxyl" as used herein, means an —OH group.

The term "hydroxy poly ethylene glycoxyalky" as used herein, refers to $H(OCH_2CH_2)_nO$-moiety appended to the parent molecule moiety through an alkyl group; wherein n=1-100. In some embodiments, n is 1-10, 1-20, or 1-50.

The term "methyl ether poly ethylene glycoxyalky" as used herein, refers to $CH_3(OCH_2CH_2)_nO$— moiety appended to the parent molecule moiety through an alkyl group; wherein n=1-100. In some embodiments, n is 1-10, 1-20, or 1-50.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

Disclosed are compounds of formula (I):

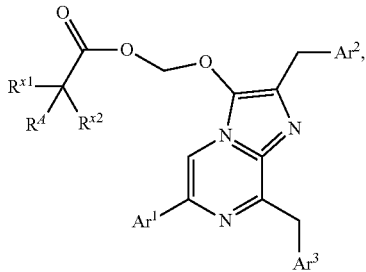

(I)

or a tautomer, or a salt thereof, wherein $Ar^1$, $Ar^2$, and $Ar^3$ are each independently selected from the group consisting of aryl and heteroaryl, wherein $Ar^1$, $Ar^2$, and $Ar^3$ are each optionally substituted; $R^A$ is selected from the group consisting of $C_2$-$C_{10}$ linear or branched alkyl, alkoxy, alkoxyalkyl, amido, acetoxy, methyl ether polyethylene glycoxy, methyl ether polyethylene glycoxyalkyl, haloalkyl, haloalkoxy, aryl, arylalkyl, cycloalkyl, hydroxyl alkyl, hydroxyl polyethylene glycoxyl, carboxyalkyl, heteroaryl, heteroarylalkyl, heterocycle, and heterocylic alkyl; $R^{x1}$, $R^{x2}$, at each occurrence, are each independently selected from the group consisting of $C_1$-$C_6$ linear or branched alkyl, optionally substituted by one or more substitutents selected from the goup consisting of alkoxy, aryl, cycloalkyl, heteroaryl, and heterocycle.

Disclosed are compounds of formula (II):

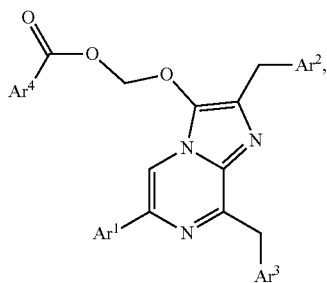

(II)

or a tautomer, or a salt thereof, wherein, $Ar^1$, $Ar^2$, and $Ar^3$ are each independently selected from the group consisting of aryl and heteroaryl, wherein $Ar^1$, $Ar^2$, and $Ar^3$ are each optionally substituted; $Ar^4$ is aryl, furan or thiophene, optionally substituted by one or more substitutents selected from the goup consisting of alkyl, alkoxy, aryl, cycloalkyl, heteroaryl, and heterocycle.

Disclosed are compounds of formula (III):

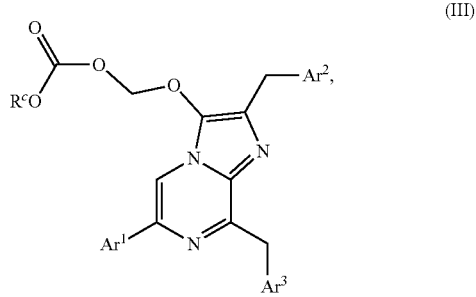

(III)

or a tautomer, or a salt thereof, wherein, $Ar^1$, $Ar^2$, and $Ar^3$ are each independently selected from the group consisting of aryl and heteroaryl, wherein $Ar^1$, $Ar^2$, and $Ar^3$ are each optionally substituted; $R^C$ is selected from the group consisting of $C_1$-$C_9$ linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocylic alkyl.

In certain embodiments, $Ar^1$ is phenyl, $Ar^2$ is furyl, and $Ar^3$ is phenyl.

In certain embodiments, $R^{x1}$ is methyl. In certain embodiments, $R^{x2}$ is methyl. In certain embodiments, both $R^{x1}$ and $R^{x2}$ are methyl.

In certain embodiments, $R^A$ is $R^BCH_2$—; wherein $R^B$ is selected from the group consisting of $C_1$-$C_9$ linear or branched alkyl, alkoxy, alkoxyalkyl, amido, acetoxy, methyl ether polyethylene glycoxy, methyl ether polyethylene glycoxyalkyl, haloalkyl, haloalkoxy, aryl, arylalkyl, cycloalkyl, hydroxyl alkyl, hydroxyl polyethylene glycoxyl, carboxyalkyl, heteroaryl, heteroarylalkyl, heterocycle, and heterocylic alkyl.

In certain embodiments, $R^A$ is $R^CO$—; wherein $R^C$ is selected from the group consisting of $C_1$-$C_9$ linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocylic alkyl.

In certain embodiments, $R^A$ is $R^CC(O)NH$—; wherein $R^C$ is selected from the group consisting of $C_1$-$C_9$ linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocylic alkyl.

In certain embodiments, $R^A$ is $R^CC(O)O$—; wherein $R^C$ is selected from the group consisting of $C_1$-$C_9$ linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocylic alkyl;

In certain embodiments, $R^A$ is $CH_3(OCH_2CH_2)_nO$—; wherein n is any number from 0-10.

In certain embodiments, $R^A$ is $CH_3(OCH_2CH_2)_nO$—; wherein n is any number from 0-10; $Ar^1$ is phenyl, $Ar^2$ is furyl, and $Ar^3$ is phenyl.

In certain embodiments, $R^A$ is $CH_3(OCH_2CH_2)_nOCH_2$—; wherein n is any number from 0-10; $A^1$ is phenyl, $Ar^2$ is furyl, and $Ar^3$ is phenyl.

In certain embodiments, $R^{x1}$ and $R^{x2}$ are methyl, and $R^A$ is $R^BCH_2$—, $R^CO$—, $R^CC(O)NH$—, $R^CC(O)O$—, $CH_3(OCH_2CH_2)_nO$—, or $CH_3(OCH_2CH_2)_nOCH_2$— as defined above.

In certain embodiments, $R^A$—$C(R^{x1}R^{x2})$— has formula:

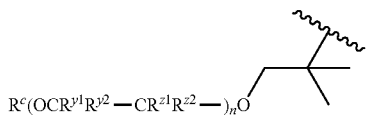

wherein $R^{y1}$, $R^{y2}$, $R^{z1}$, and $R^{z2}$, at each occurrence, are each independently selected from the group consisting of hydrogen and $C_1$-$C_6$-alkyl, optionally substituted by one or more substitutuents selected from the goup consisting of halo, alkoxy, haloalkoxy, aryl, cycloalkyl, heteroaryl, and heterocycle; and n is any number from 0-10; and wherein $R^C$ is selected from the group consisting of $C_1$-$C_9$ linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocylic alkyl.

In certain embodiments, $R^A$—$C(R^{x1}R^{x2})$— has formula:

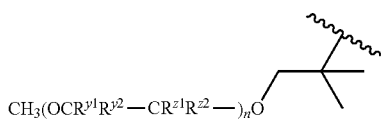

wherein $R^{y1}$, $R^{y2}$, $R^{z1}$, and $R^{z2}$ are as defined above.

In certain embodiments, $R^A$—$C(R^{x1}R^{x2})$— has formula:

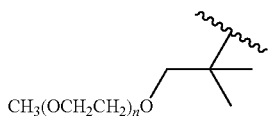

wherein n is 0-10.

In certain embodiments, $R^A$—$C(R^{x1}R^{x2})$— has formula:

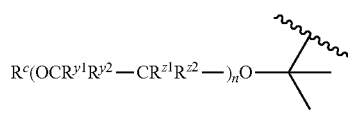

wherein $R^{y1}$, $R^{y2}$, $R^{z1}$, and $R^{z2}$ are as defined above, and n is 0-10.

In certain embodiments, $R^A$—$C(R^{x1}R^{x2})$— has formula:

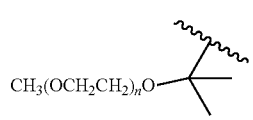

wherein n is 0-10.

In certain embodiments, $R^A$—$C(R^{x1}R^{x2})$— is selected from the group consisting of:

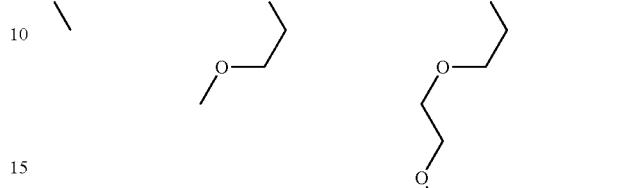

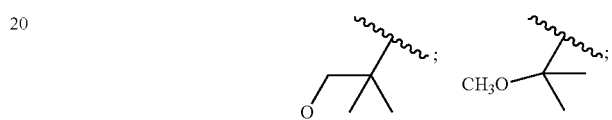

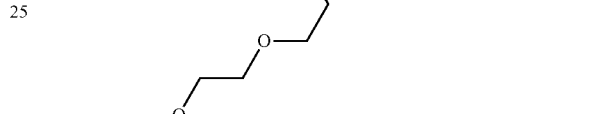

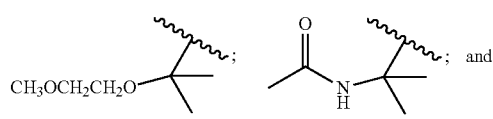

In certain embodiments, the compound of formula (I) has formula (I-a):

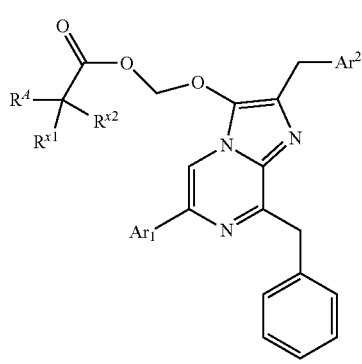

(I-a)

wherein $R^A$, $R^{x1}$, $R^{x2}$, $Ar^1$, and $Ar^2$ are as defined above.

In certain embodiments, the compound of formula (I) has formula (I-b):

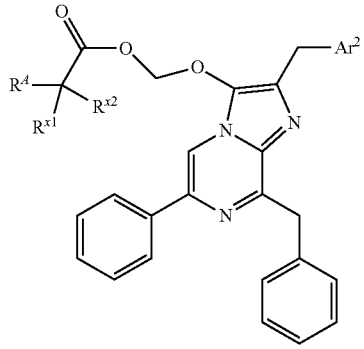

(I-b)

wherein $R^4$, $R^{x1}$, $R^{x2}$, and $Ar^2$ are as defined above.

In certain embodiments, the compound of formula (I) has formula (I-c):

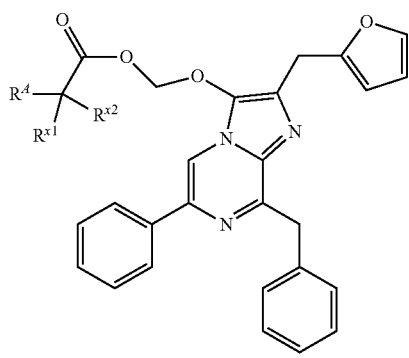

(I-c)

wherein $R^4$, $R^{x1}$, and $R^{x2}$, are as defined above.

In certain embodiments, the compound of formula (I) has formula (I-d):

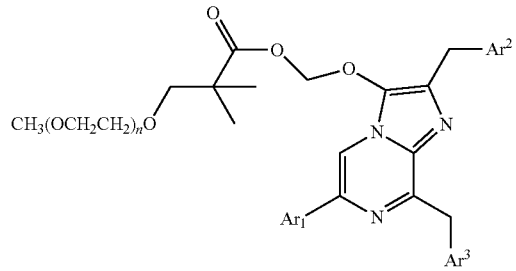

(I-d)

wherein $Ar^1$, $Ar^2$, $Ar^3$, and n are as defined above.

In certain embodiments, the compound of formula (I) has formula (I-e):

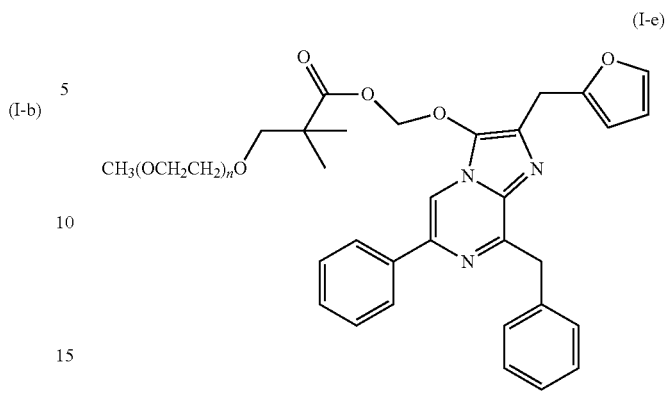

(I-e)

wherein n is as defined above. In some embodiments, n is any number from 0-10.

In certain embodiments, the compound of formula (I) has formula (I-f):

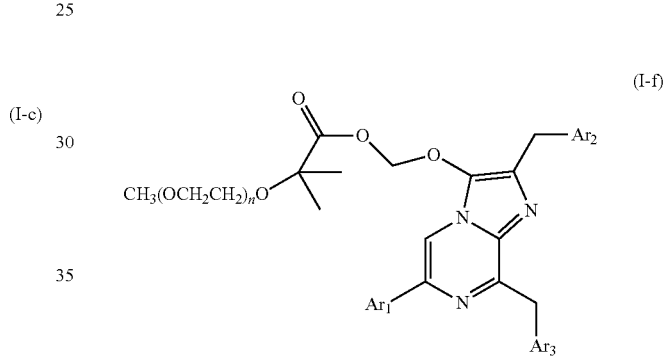

(I-f)

wherein $Ar^1$, $Ar^2$, $Ar^3$, and n are as defined above.

In certain embodiments, the compound of formula (I) has formula (I-g):

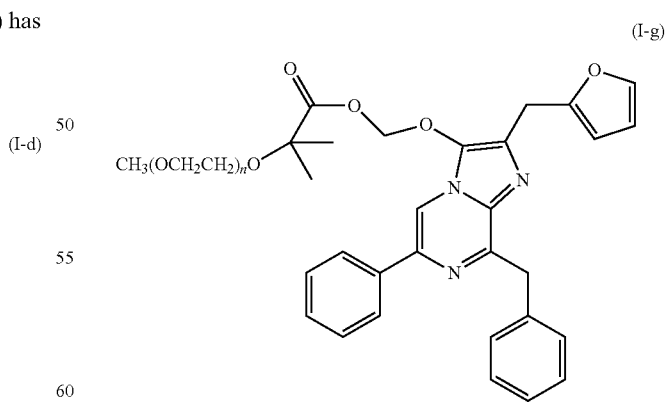

(I-g)

wherein n is as defined above. In some embodiments, n is any number from 0-10.

In certain embodiments, the compound of formula (I) has formula (I-h):

(I-h)

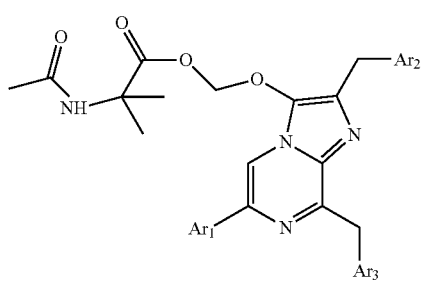

wherein Ar¹, Ar², and Ar³, are as defined above.

In certain embodiments, the compound of formula (I) has formula (I-i):

(I-i)

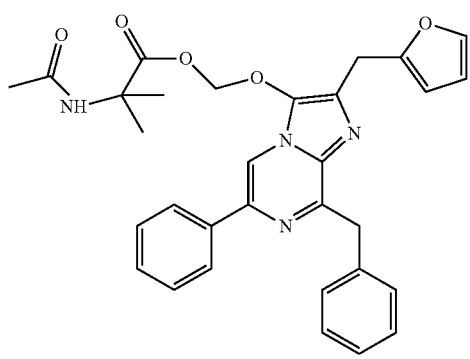

In certain embodiments, the compound of formula (I) has formula (I-j):

(I-j)

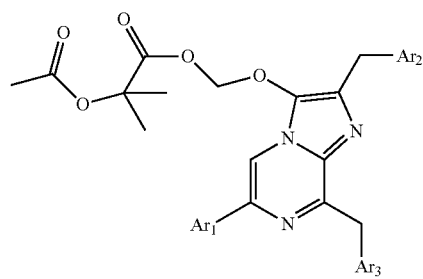

wherein Ar¹, Ar², and Ar³ are as defined above.

In certain embodiments, the compound of formula (I) has formula (I-k):

(I-k)

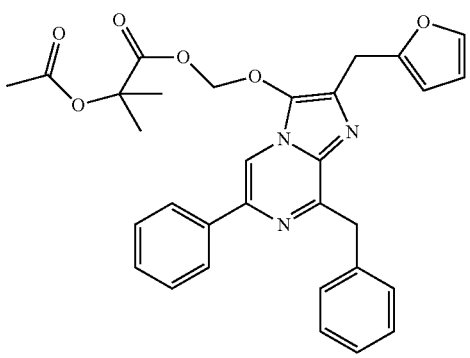

In certain embodiments, Ar⁴ is phenyl, furan or thiophene, optionally substituted by one or more alkyoxy substituents.

In certain embodiments, Ar⁴ is phenyl, furan or thiophene, optionally substituted by one or more alkyoxy substituents; Ar¹ is phenyl, Ar² is furyl, and Ar³ is phenyl.

In certain embodiments, the compound of formula (II) has formula (II-a):

(II-a)

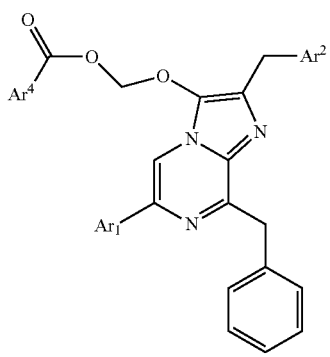

wherein Ar¹, Ar², and Ar⁴ are as defined above.

In certain embodiments, the compound of formula (II) has formula (II-b):

(II-b)

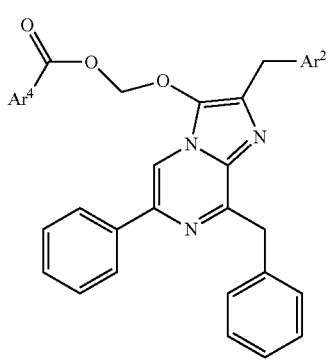

wherein Ar¹ and Ar⁴ are as defined above.

In certain embodiments, the compound of formula (II) has formula (II-c):

(II-c)

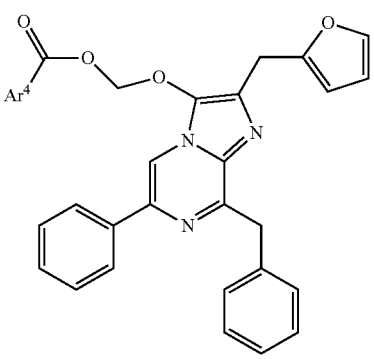

wherein Ar⁴ is as defined above.

In certain embodiments, the compound of formula (III) is carbonate, wherein $R^C$ is selected from the group consisting of $C_1$-$C_9$ linear or branched alkyl, alkoxyalkyl, aryl, arylalkyl, cycloalkyl, hydroxyl alkyl, heteroaryl, heteroarylalkyl, heterocycle, and heterocyclic alkyl.

In certain embodiments, the compound of formula (III) is carbonate, wherein $R^C$ is selected from the group consisting of $C_1$-$C_9$ linear or branched alkyl, alkoxyalkyl, aryl, arylalkyl, cycloalkyl, hydroxyl alkyl, heteroaryl, heteroarylalkyl, heterocycle, and heterocyclic alkyl; wherein $Ar^1$ is phenyl, $Ar^2$ is furyl, and $Ar^3$ is phenyl.

In certain embodiments, the compound of formula (III) has formula (III-a):

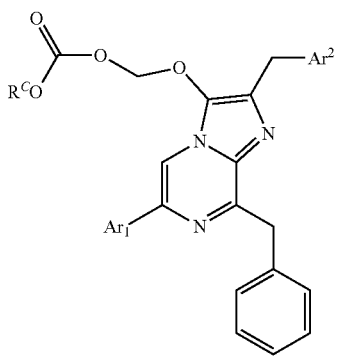

(III-a)

wherein $Ar^1$, $Ar^2$, and $R^C$ are as defined above.

In certain embodiments, the compound of formula (III) has formula (III-b):

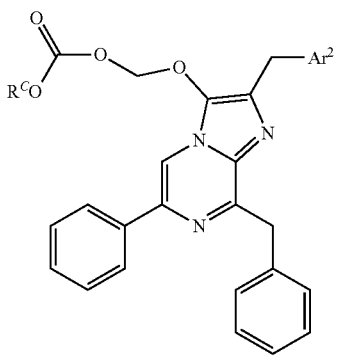

(III-b)

wherein $Ar^2$ and $R^C$ are as defined above.

In certain embodiments, the compound of formula (III) has formula (III-c):

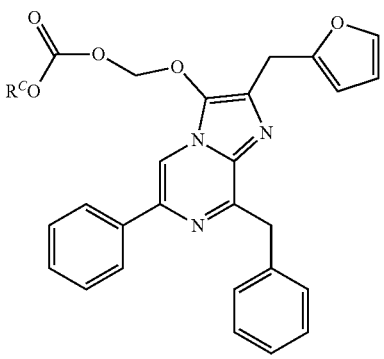

(III-c)

wherein $R^C$ is as defined above.

Representative compounds of formula (I) include, but are not limited to:

((8-benzyl-2-(furan-2-ylmethyl)-6-phenylimidazo[1,2-a]pyrazin-3-yl)oxy)methyl 3-methoxy-2,2-dimethylpropanoate (WZ-0323);

((8-benzyl-2-(furan-2-ylmethyl)-6-phenylimidazo[1,2-a]pyrazin-3-yl)oxy)methyl 3-(2-(2-methoxyethoxy)ethoxy)-2,2-dimethylpropanoate (WZ-0324);

((8-benzyl-2-(furan-2-ylmethyl)-6-phenylimidazo[1,2-a]pyrazin-3-yl)oxy)methyl 3-(2-methoxyethoxy)-2,2-dimethylpropanoate (WZ-0333);

((8-benzyl-2-(furan-2-ylmethyl)-6-phenylimidazo[1,2-a]pyrazin-3-yl)oxy)methyl 13,13-dimethyl-2,5,8,11-tetraoxatetradecan-14-oate (WZ-0336);

((8-benzyl-2-(furan-2-ylmethyl)-6-phenylimidazo[1,2-a]pyrazin-3-yl)oxy)methyl 16,16-dimethyl-2,5,8,11,14-pentaoxaheptadecan-17-oate (WZ-0364);

((8-benzyl-2-(furan-2-ylmethyl)-6-phenylimidazo[1,2-a]pyrazin-3-yl)oxy)methyl 2-methoxy-2-methylpropanoate (WZ-0451); and ((8-benzyl-2-(furan-2-ylmethyl)-6-phenylimidazo[1,2-a]pyrazin-3-yl)oxy)methyl 2-acetamido-2-methylpropanoate (WZ-0467).

Representative compounds of formula (II) include, but are not limited to:

((8-benzyl-2-(furan-2-ylmethyl)-6-phenylimidazo[1,2-a]pyrazin-3-yl)oxy)methyl furan-2-carboxylate (WZ-0420);

((8-benzyl-2-(furan-2-ylmethyl)-6-phenylimidazo[1,2-a]pyrazin-3-yl)oxy)methyl furan-3-carboxylate (WZ-0461); and ((8-benzyl-2-(furan-2-ylmethyl)-6-phenylimidazo[1,2-a]pyrazin-3-yl)oxy)methyl benzoate (WZ-0416);

Representative compounds of formula (III) include, but are not limited to:

((8-benzyl-2-(furan-2-ylmethyl)-6-phenylimidazo[1,2-a]pyrazin-3-yl)oxy)methyl methyl carbonate (WZ-0419).

Compound names are assigned by using Struct=Name naming algorithm as part of CHEMDRAW® ULTRA v. 12.0.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds

The compounds of formula (I), formula (II), and (III) may be pro-substrates of luciferases to produce luminescence upon actions of non-luciferase enzymes present in cells, added in extracellular media, or in the sample to release the luciferase substrate (such as coelenterazine or furimazine) over a certain time period. In some embodiments, the compounds may react with a deprotection enzyme (such as an esterase) to release the luciferase substrate. The compounds may have improved stability, improved water solubility, improved cell permeability, reduced autoluminescence, and/or reduced toxicity. In some embodiments, the disclosed compounds may exhibit unexpectedly superior serum stability in comparison to other coelenterzine and furimazine ester analogues. In particular embodiments, the disclosed compounds are stable in a media containg a serum, which allows for a stable signal in various live cell assays up to 24 hours and longer.

Pro-coelenterazine analogues, as used herein, include pro-coelenterazine and pro-furimazine compounds, which have been structurally modified from coelenterazine and furimazine, respectively, such that they no longer interact with a luminogenic protein to luminesce. In some embodiments, the structure modification may be an addition of an enzyme-removable group (such as formation of an ester group). Interaction of the pro-coelenterazine analogues with an appropriate enzyme (such as an esterase) may yield an active luminophore compound, including coelenterazine, furimazine, or derivatives thereof. The enzyme which converts the pro-coelenterazine analogue into a luminophore is preferably a non-luminogenic enzyme. In some embodiments, the disclosed compounds of formula (I) include pro-coelenterazines or pro-furimazines compounds, which may be converted into ester protected luminophores.

In general, "enhanced" or "improved" means that the particular property (such as luminescence, and signal stability) is increased relative to that of the reference luciferase plus coelenterazine analogue combination or coelenterazine analogue under consideration, where the increase is at least 1%, at least 5%, at least 10%, at least 20%, at least 25%, at least 50%, at least 75%, at least 90%, at least 100%, at least 200%, at least 500%, or at least 1000% greater than the reference luciferase plus coelenterazine combination or coelenterazine analogue under consideration; or the reference unsubstituted acetyl ester linked to coelenterazine through methylene ether bond.

"Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the pro-coelenterazine substrate.

The luminescence reaction in various embodiments is carried out in a solution. In other embodiments, the luminescence reaction is carried out on a solid support. In some embodiments, the solution may contain live cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., pro-coelenterazine analogue, buffer, etc., into a reaction chamber (e.g., a well of a multiwell plate such as a 96-well plate) containing the ester deprotection enzyme and the luminescent protein. In still other embodiments, the luciferase and/or pro-coelenterazine analogues (e.g., compounds of formula (I)) are introduced into a host, and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

The disclosed compounds can include properties such as enhanced physical stability or reduced autoluminescence. The physical stability of the present compounds refers to how stable a compound is in certain conditions such that it maintains the ability to luminesce when used as a substrate by a luciferase. Luminescence that is not dependent on the activity of a luciferase or photoprotein is termed autoluminescence. Autoluminescence is the luminescence of a substance produced by energy released in the form of light during decay or decomposition. For example, autoluminescence can be caused by spontaneous oxidation of the luminogenic substrate coelenterazine.

For a pro-coelenterazine compound, "stability" may also refer to how stable the compound is in certain conditions such that it maintains the ability to release the coelenterazine substrate gradually over certain time period (for example, by the actions of live cell enzymes) when used for live cell assays by a luciferase. Stability for the disclosed pro-coelenterazine compounds may be demonstrated by the percentage of degradation for the particular compound in a specific environment over time. The percentage of purity for a particular compound can be determined by a variety of techniques known to those skilled in the art. These techniques include, for example, nuclear magnetic resonance (NMR) and high performance liquid chromatography (HPLC).

"Serum stability" refers to the stability of a compound in media or culture that includes serum. The serum as used herein may include, but is not limited to, fetal bovine serum (FBS). Serum stability of a compound as used herein generally may be characterized by the extent of degradation of such compound in a serum over a period of time. For example, a compound may degrade by less than 25%, less than 20%, less then 15%, or even less than 10% in FBS over a period of 24 hours or longer. For live cell assays, serum (such as FBS) is a component to maintain cell health. The degree of degradation of the disclosed compounds or the other pro-coelenterazine analogues in DMSO control, or DMEM media with/without FBS, can be monitored by HPLC using specific elution solvent/buffer (e.g. 0.1% TFA and acetonitrile) under the same condition at certain time of points. The percentage of purity can be calculated by the peak area of the tested compound divided by the total peak areas including tested compound and degradation compounds at their corresponding retention time at certain absorbance wavelength (e.g. 260 nm) at certain time point in media with/without FBS. The changes of purity for a given compound over time indicate the degree of instability of the compound in media/culture with/without serum. For example, the degradations of the disclosed compounds listed in Scheme 1a are significantly slower than other pro-coelenterazine ester analogues listed Scheme 1b.

Scheme 1a. Examples of serum stable pro-furimaze esters

WZ-0323

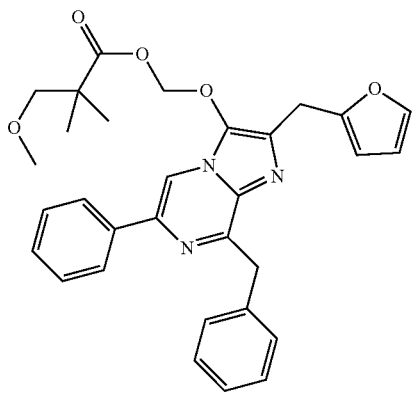

WZ-0333

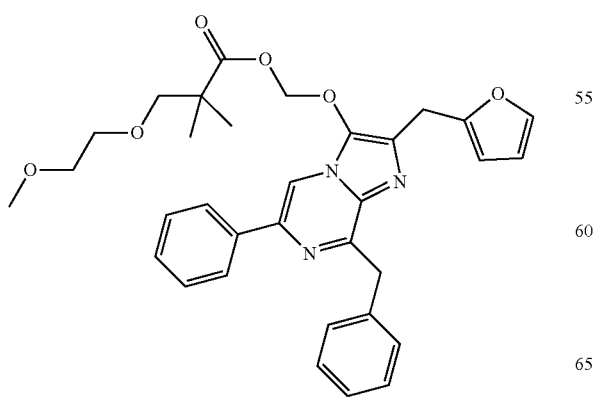

-continued

WZ-0324

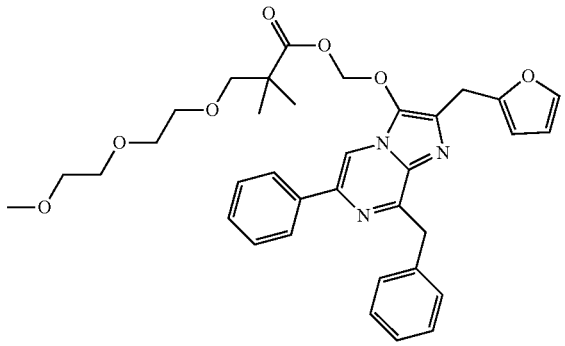

WZ-0336

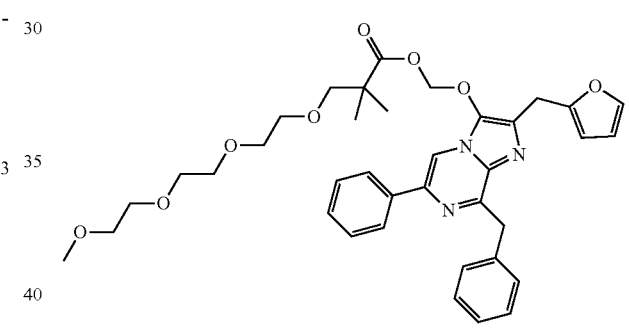

WZ-0364

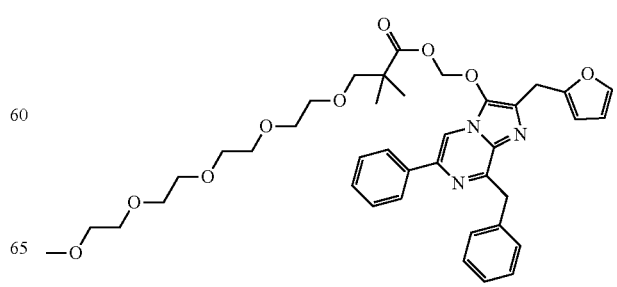

WZ-0451
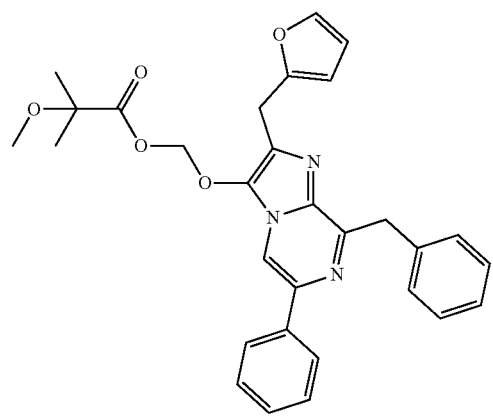
WZ-0461
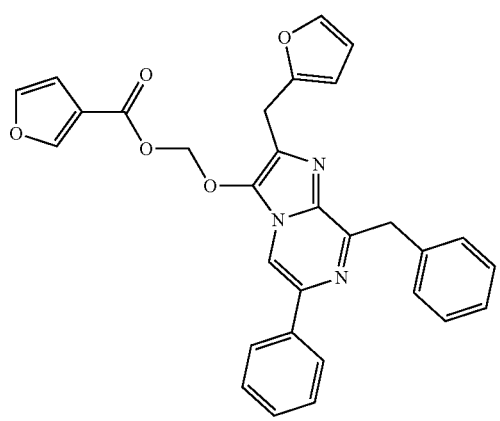
WZ-0467
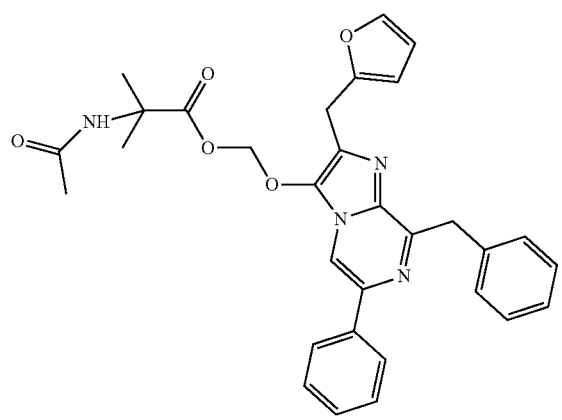
WZ-0416
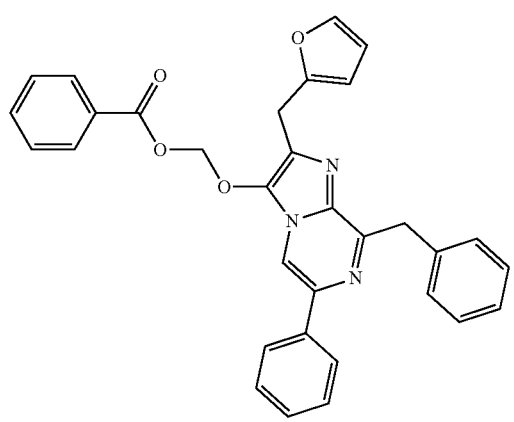
WZ-0420
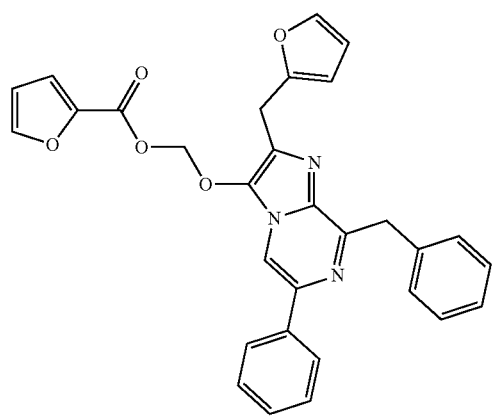
WZ-0419
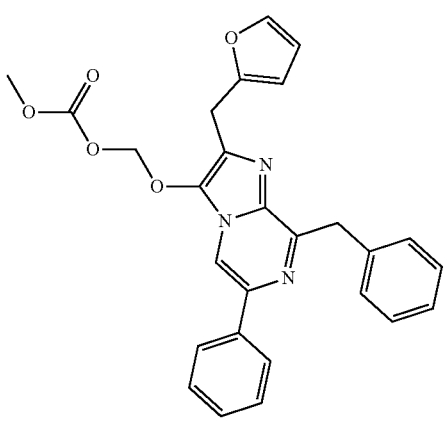

Scheme 1b. Examples of serum instable or less stable compounds
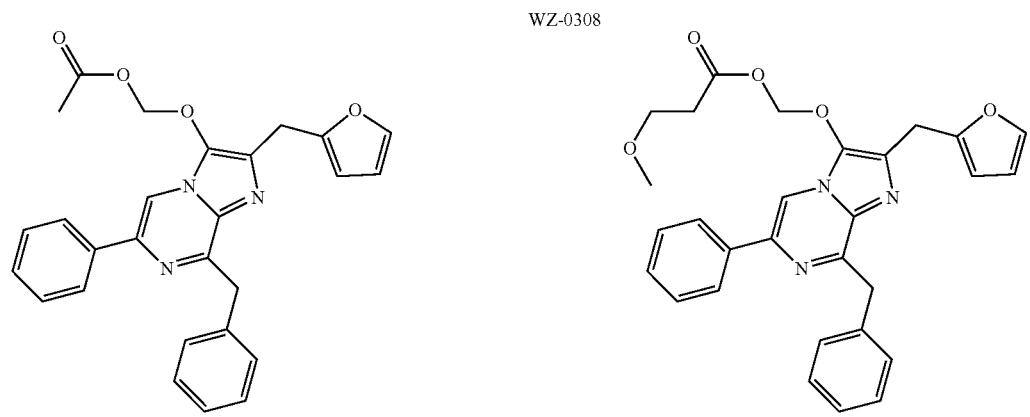
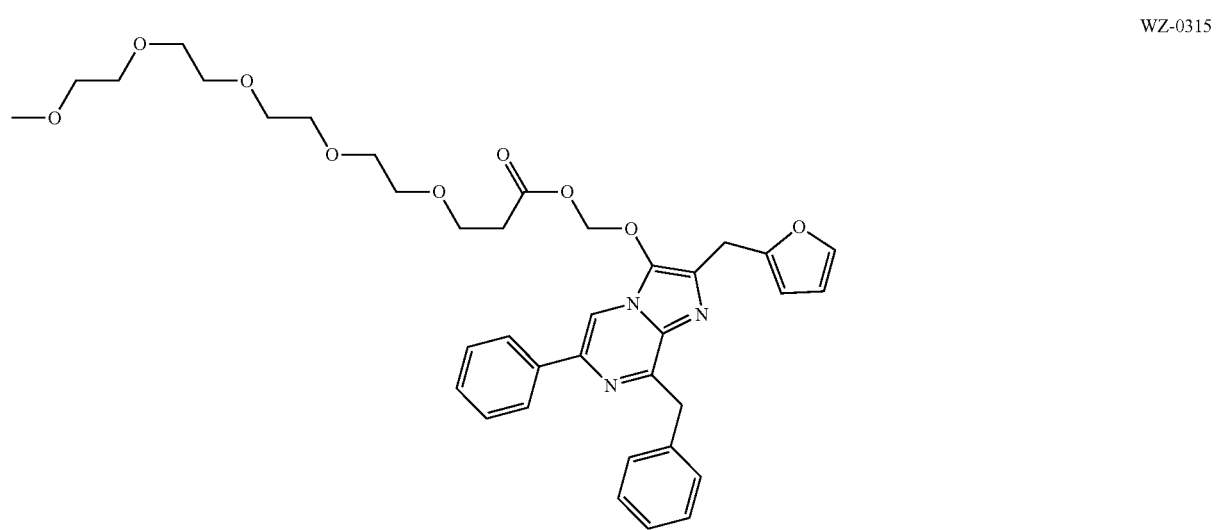
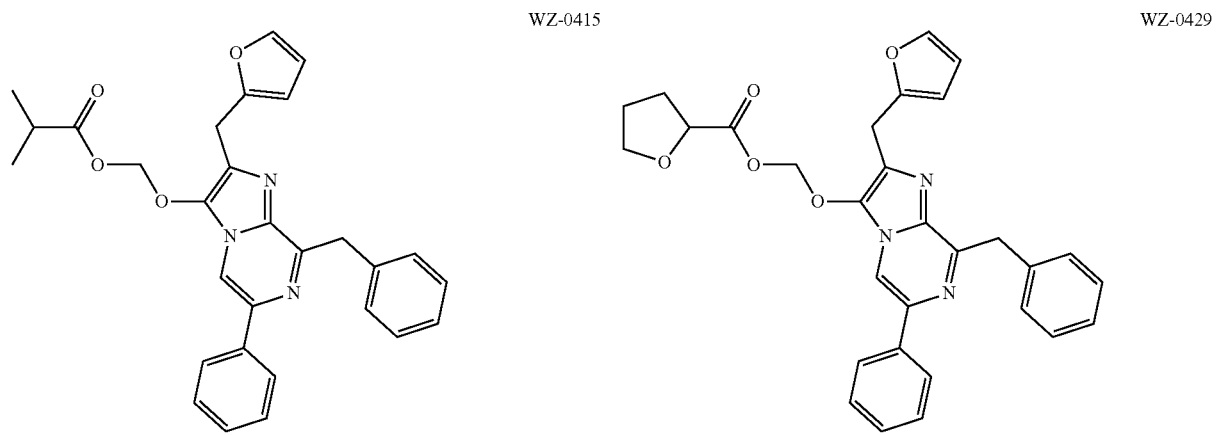

WZ-0439

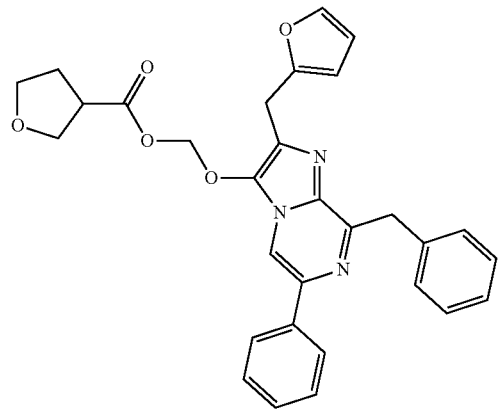

WZ-0454

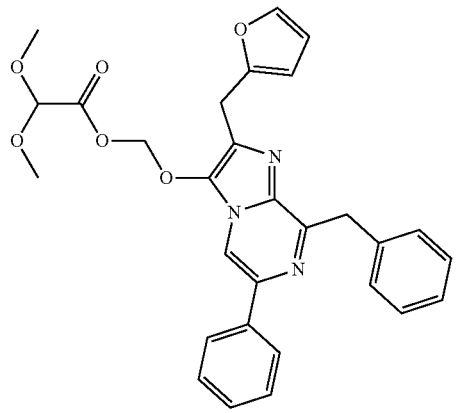

WZ-0441

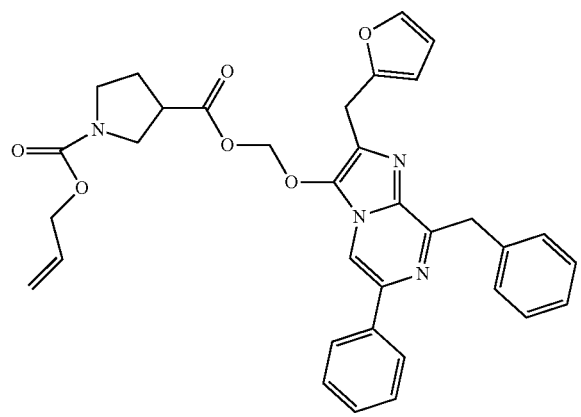

WZ-0441-2

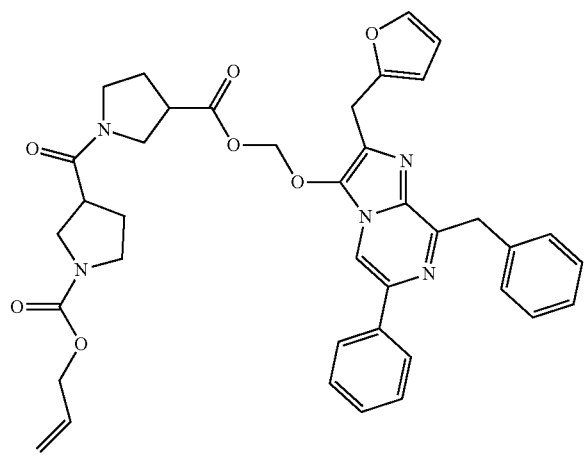

6823

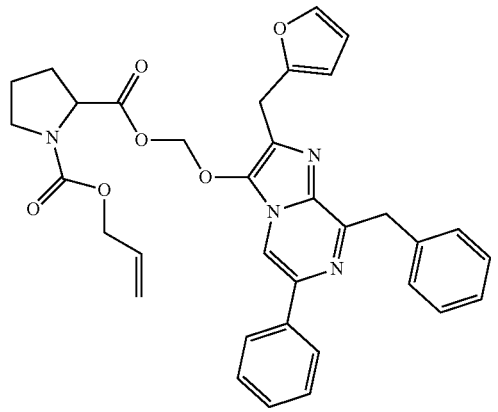

WZ-0430

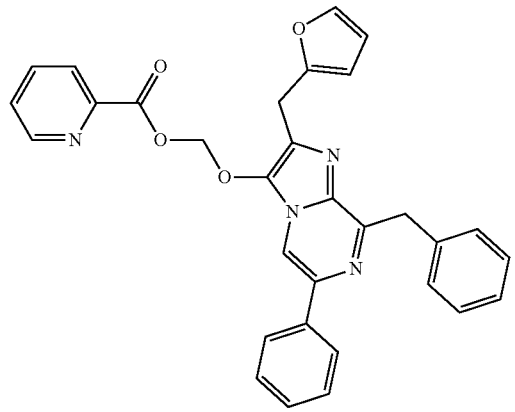

The disclosed compounds demonstrate unexpected, superior serum stability compared to other pro-coelenterazine ester compounds. In some embodiments, the present compounds may have improved serum stability (for example, <20% degraded in DMEM media with 10% FBS over 12 hours or beyond, FIGS. 2A-2I). By contrast, the other ester compounds (such as WZ-0308, WZ-0310, WZ-0315, WZ-0429, WZ-0439, WZ-0454, and WZ-0441) show poor serum stability (>80% degraded in DMEM media with 10% FBS even over 12 hours, FIGS. 1A-1H). The remarkable stability of the present compounds provides for a variety of enhancements for live cell assays. In some embodiments, the disclosed compounds can provide a stable luminescent signal that last for at least 12 hours, at least 16 hours, at least 24 hours, at least 36 hours, or at least 48 hours for live cells that express luciferase or fragment complementary luciferase in media containing FBS. Due to their improved serum stability, the present compounds can allow continuous release of active furimazine or coelenterazine molecules available for luminescent assays over a long period of time, thus improving the signal duration of the assays.

Figure 3A:
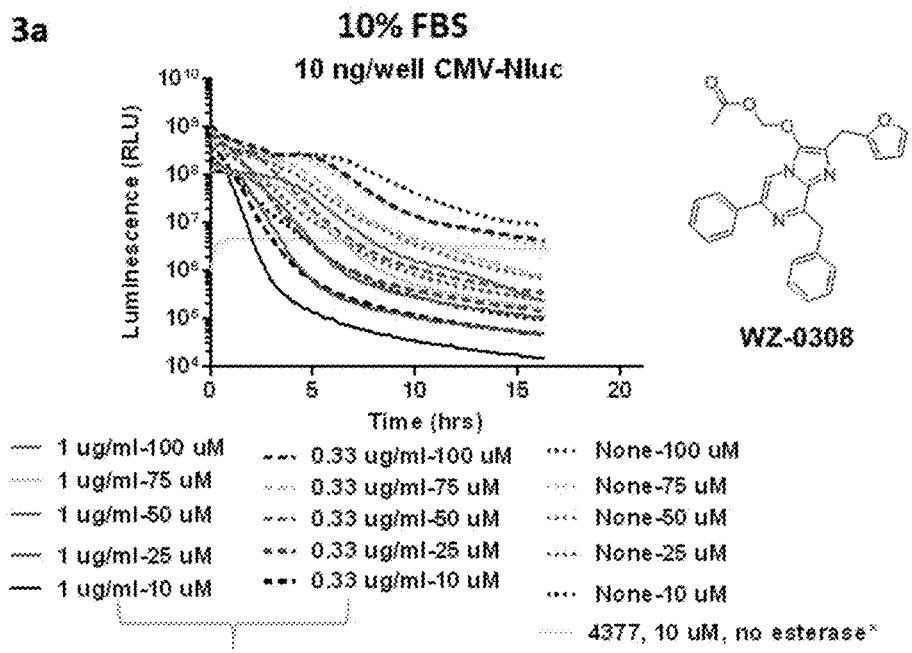
FIGS. 3A-3M show the luminescent signal decay over time in 10 ng/well of CMV promoter-NanoLuc® gene (Nluc) transfected HEK293 cells in DMEM media with 10% FBS with/without adding exogenous esterase porcine liver esterase (PLE) (FIGS. 3A-3C) or HEK293 cells expressing the PKA NanoBiT™ positive control pair to Nluc in DMEM media with 4% FBS (FIGS. 3D-3M). These include results for serum instable or less stable compounds, WZ-0308 (FIG. 3A), WZ-0415 (FIG. 3D), WZ-0429 (FIG. 3E), WZ-0439 (FIG. 3F), WZ-0454 (FIG. 3G), and WZ-0441 (FIG. 3H); results for traditional live cell pro-substrate PBI-4377 (FIG. 3B); and results for the disclosed serum stable compounds WZ-0324 (FIG. 3C), WZ-0451 (FIG. 3I), WZ-00416 (FIG. 3J), WZ-0420 (FIG. 3K), WZ-0461 (FIG. 3L), and WZ-0419 (FIG. 3M).
Figure 3B:
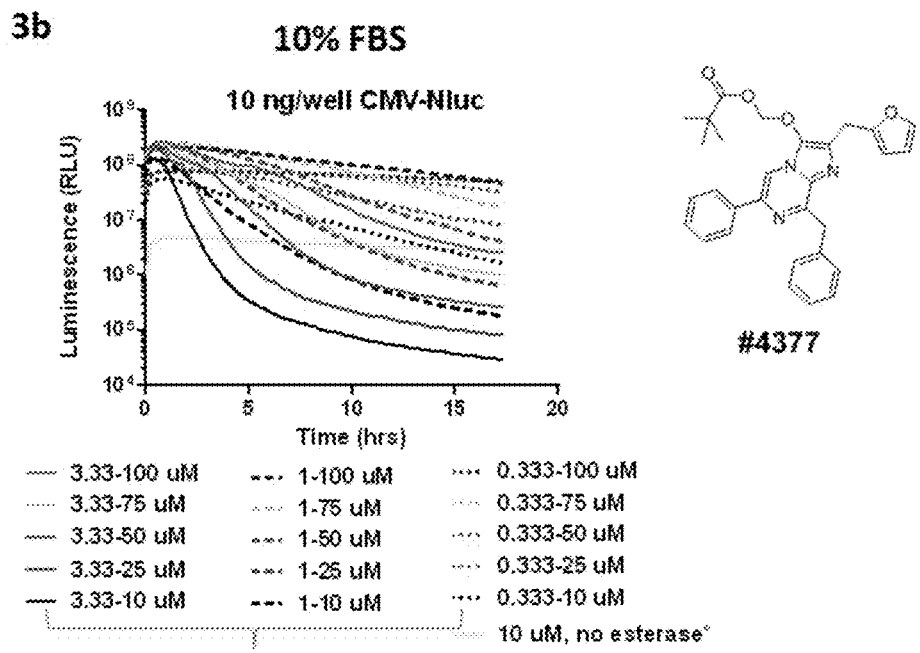
Figure 3C:
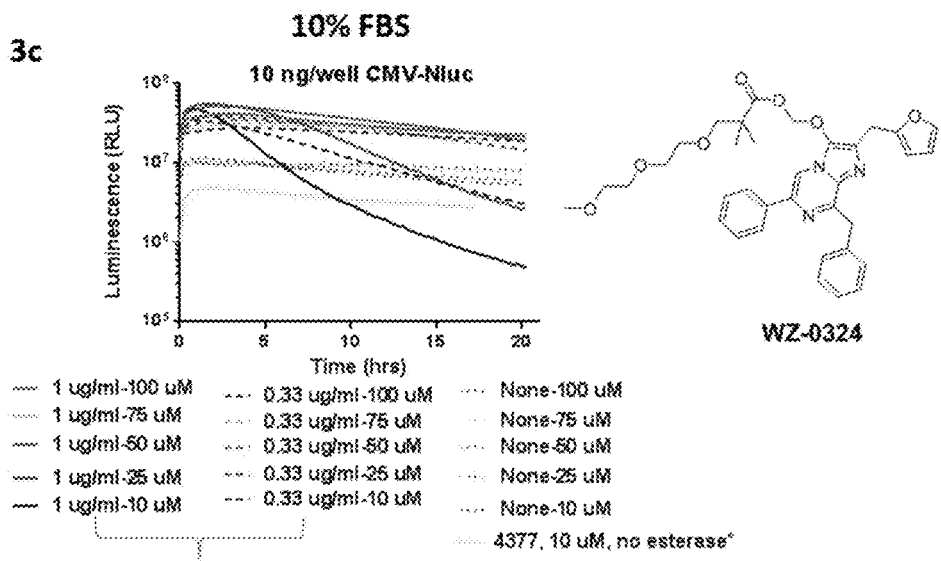
Figure 3D:
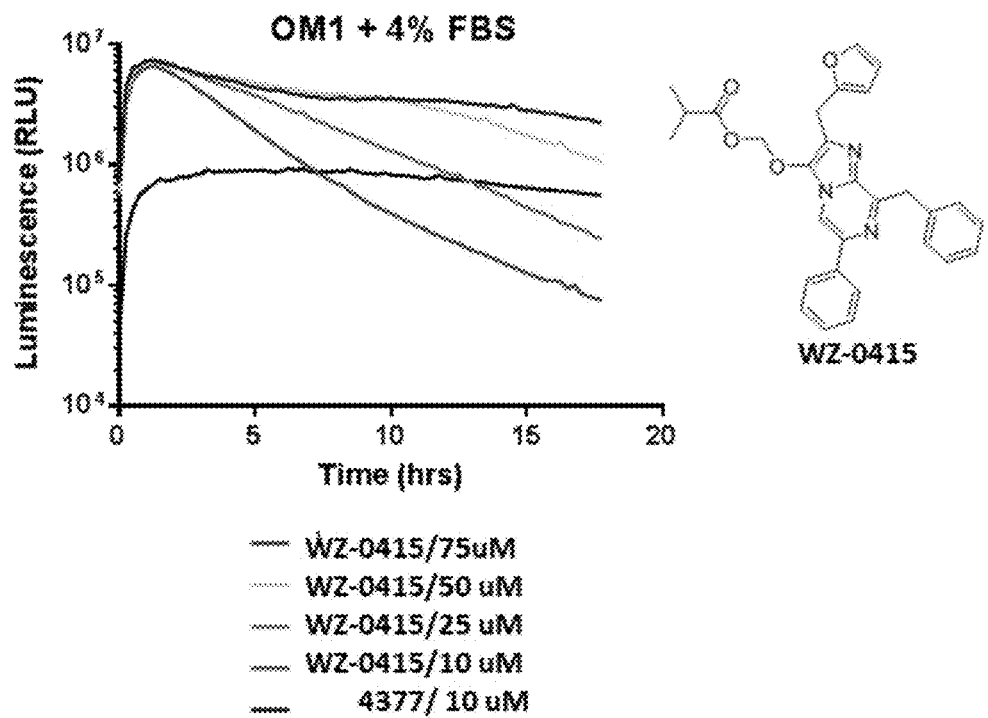
Figure 3E:
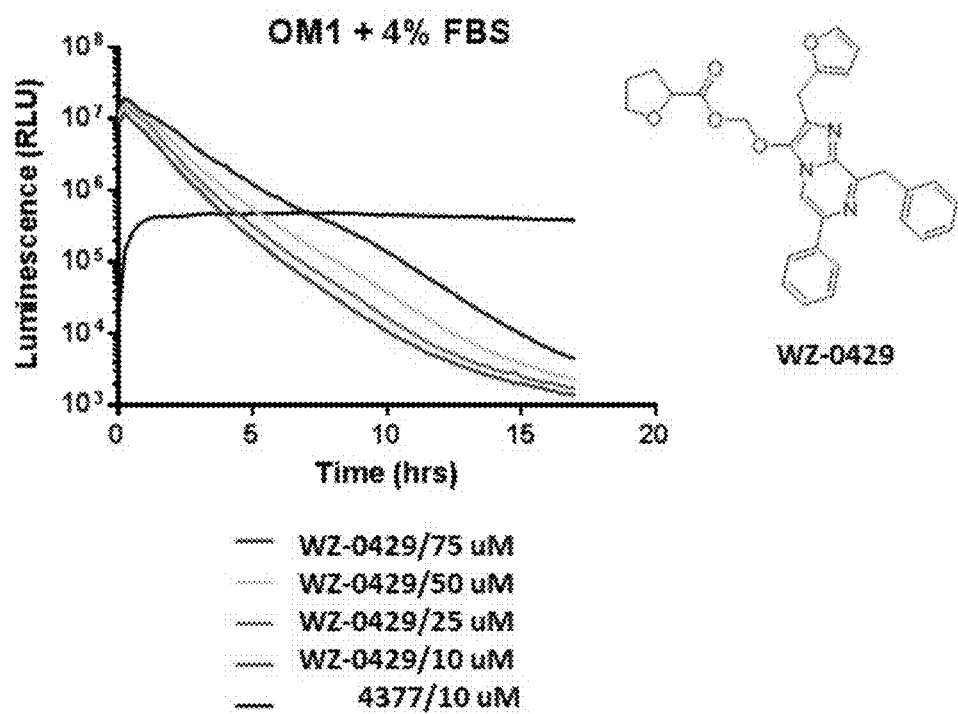
Figure 3F:
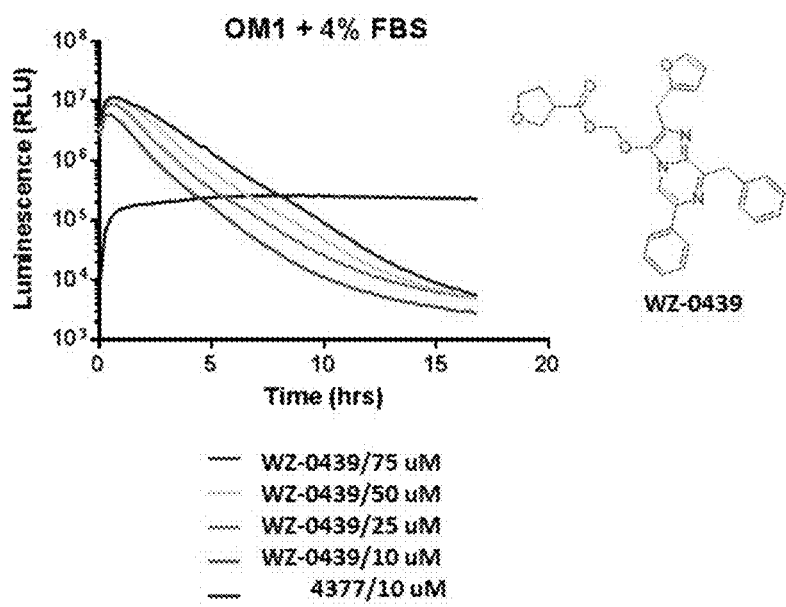
Figure 3G:
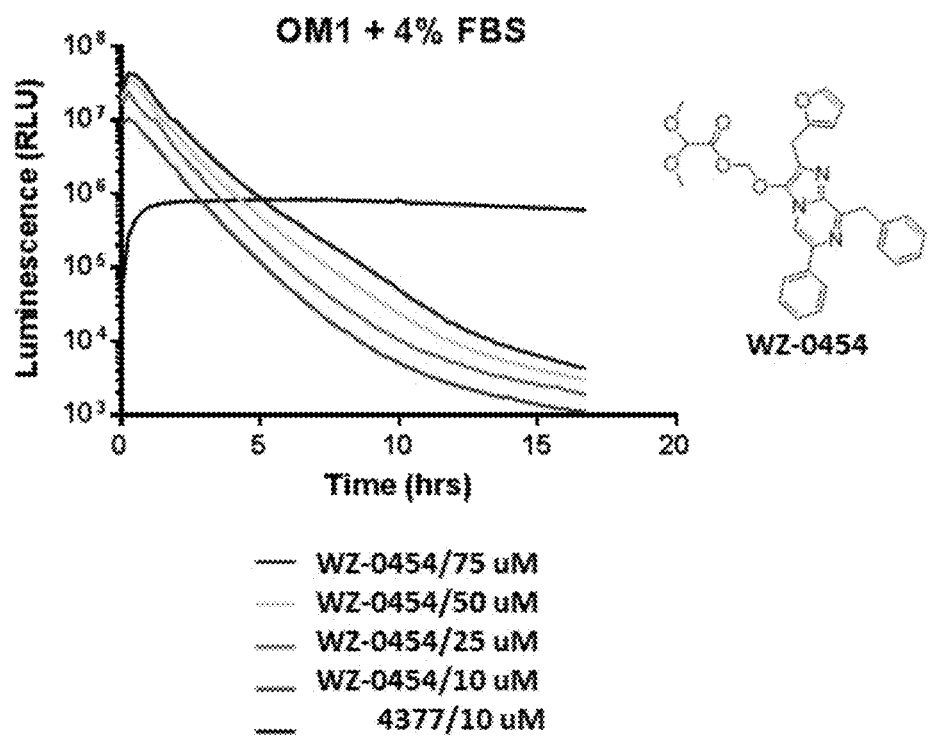
Figure 3H:
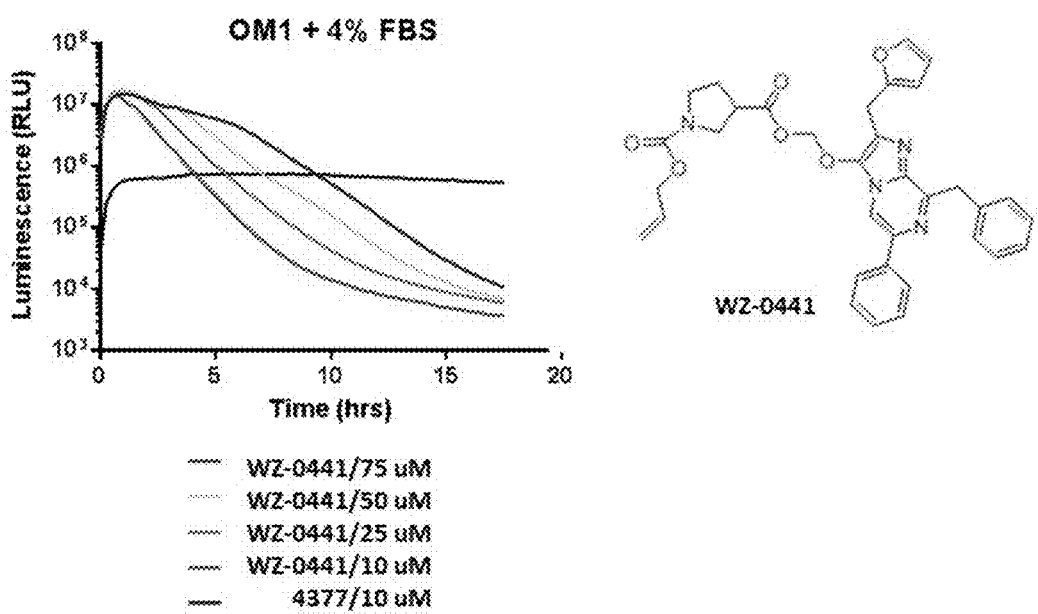
Figure 3I:
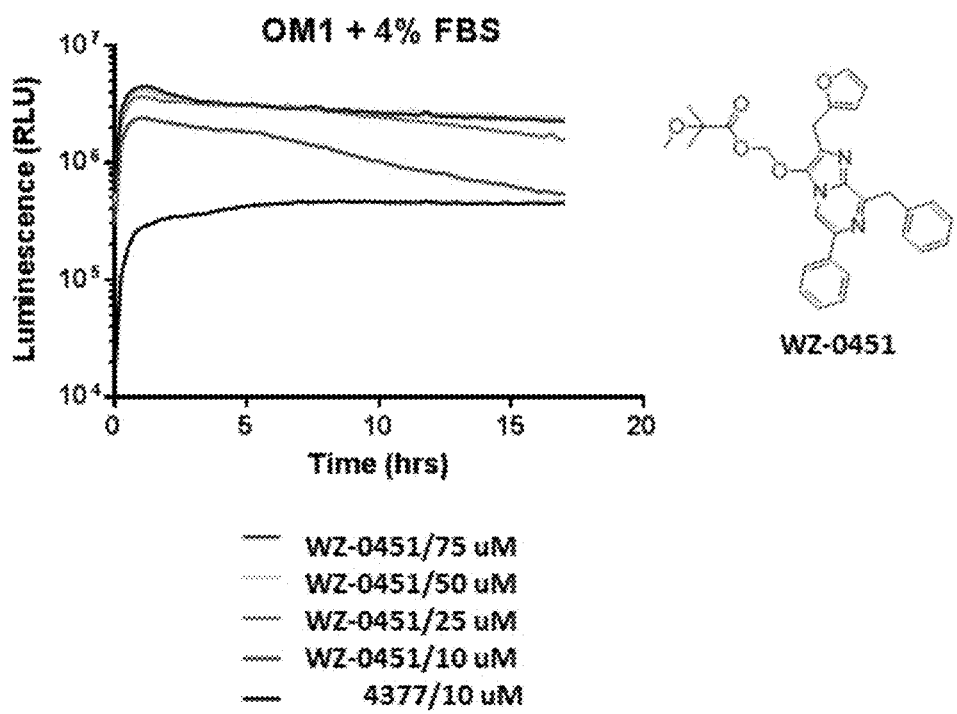
Figure 3J:
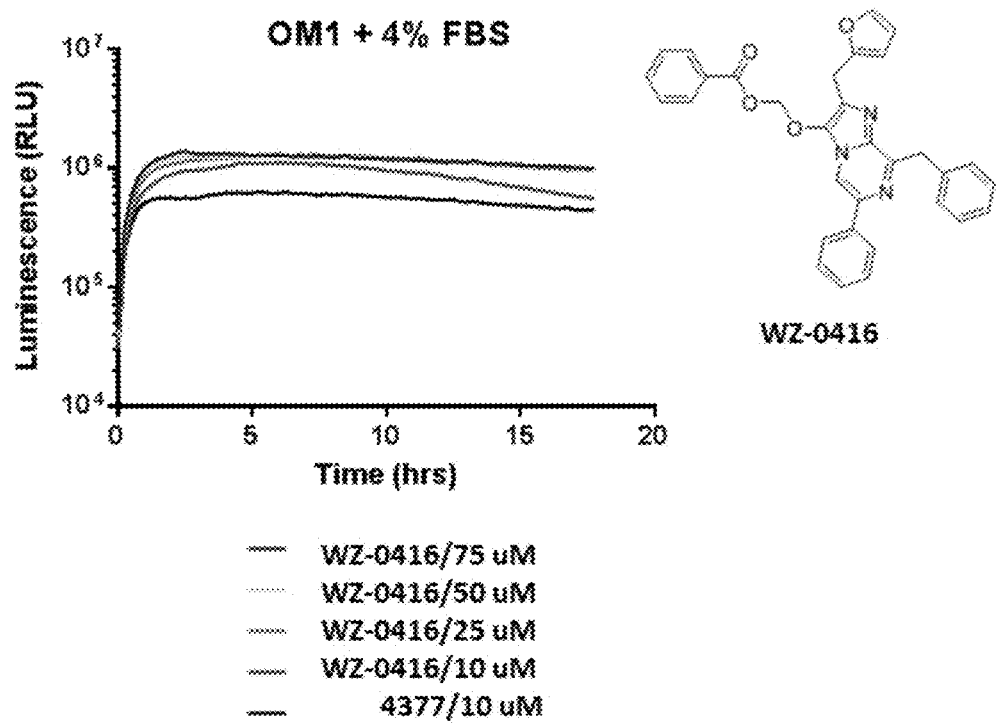
Figure 3K:
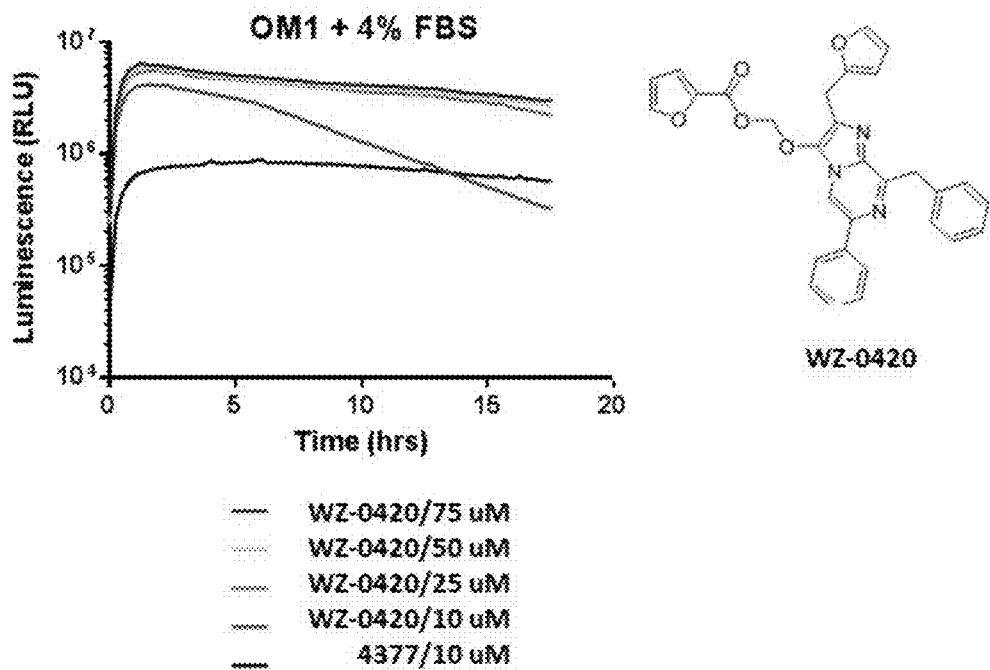
Figure 3L:
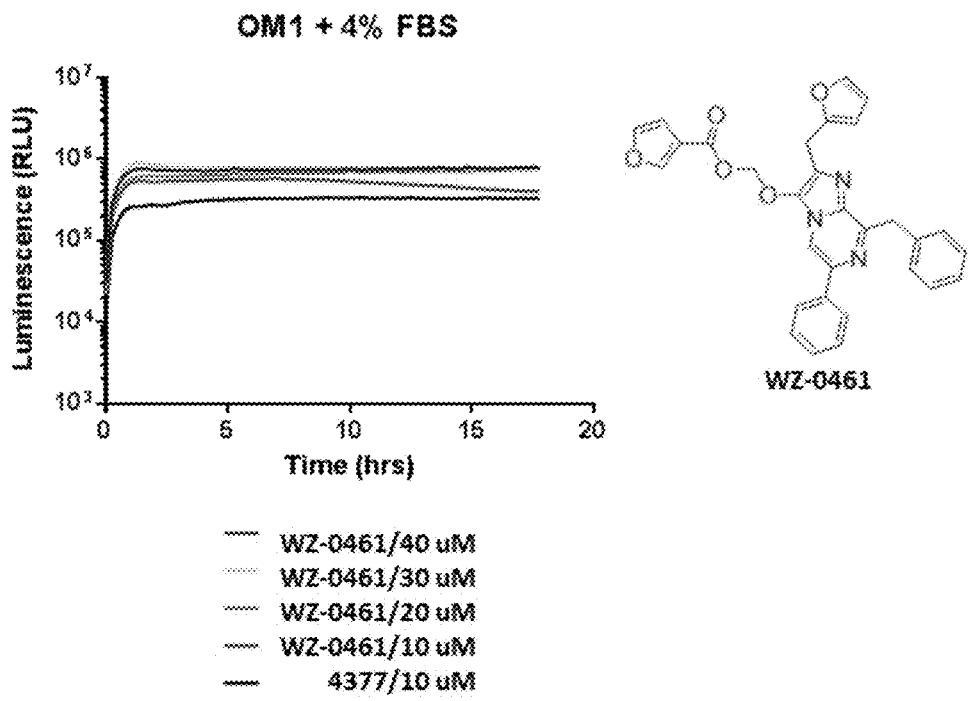
Figure 3M:
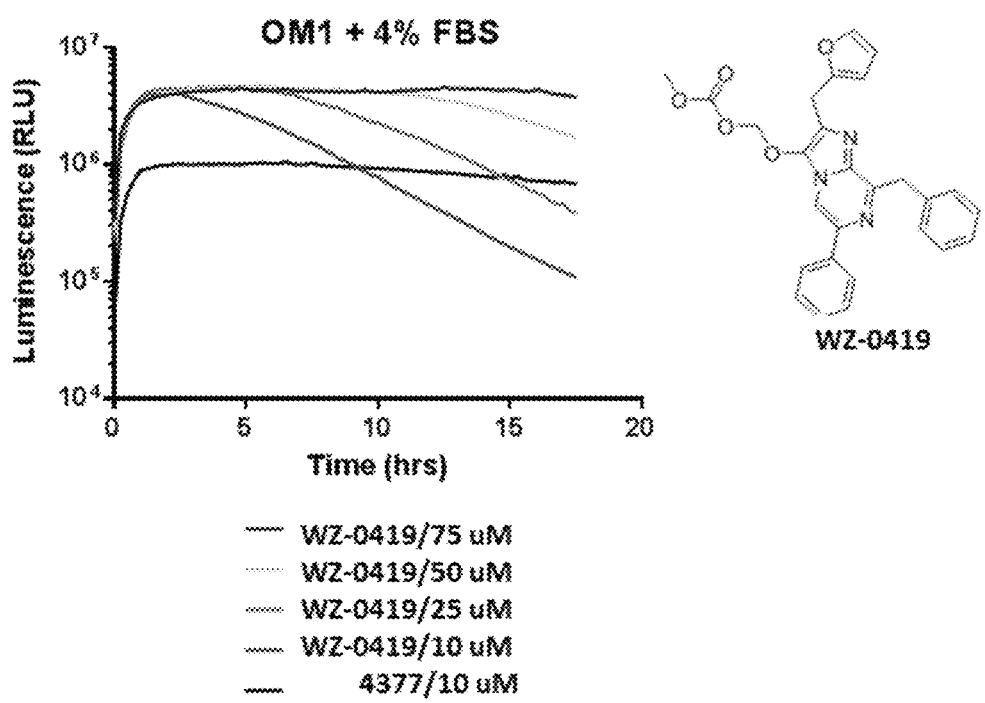
Figure 4A:
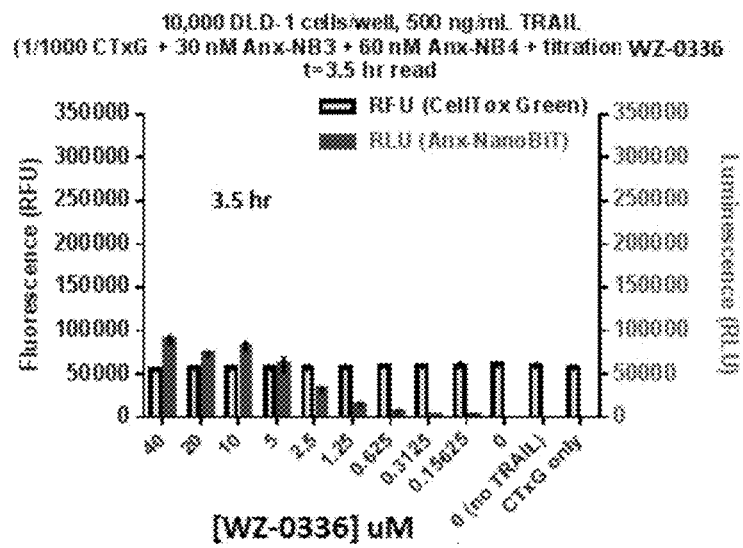
FIGS. 4A-4D show TRAIL (an extrinsic apoptosis inducer) produced dose-dependent increases in luminescence with compound WZ-0336 at different treatment time: 3.5 hours (FIG. 4A), 7.0 hours (FIG. 4B), 24 hours (FIG. 4C), and 30 hours (FIG. 4D).
Figure 4B:
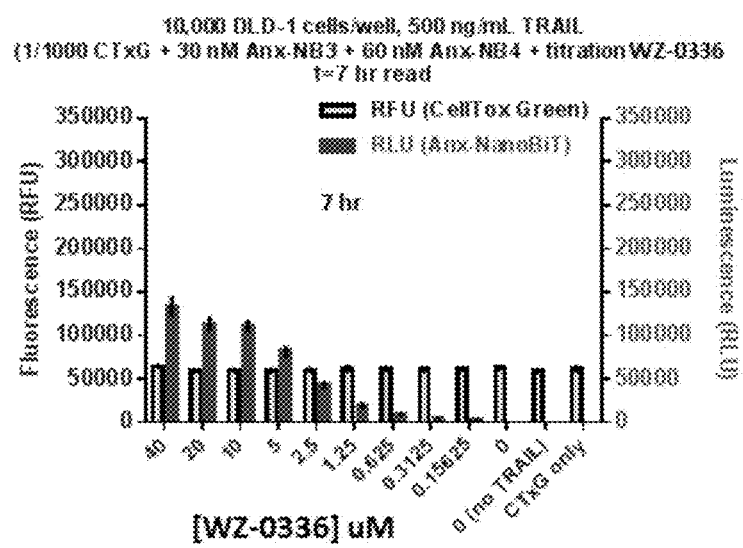
Figure 4C:
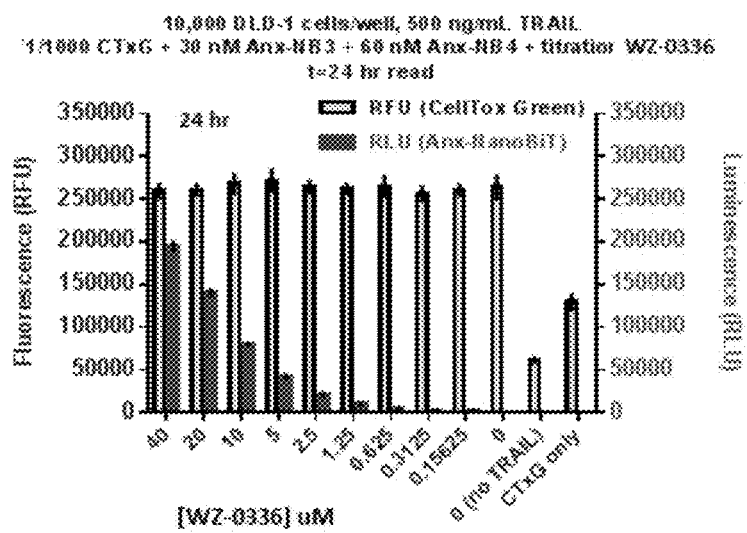
Figure 4D:
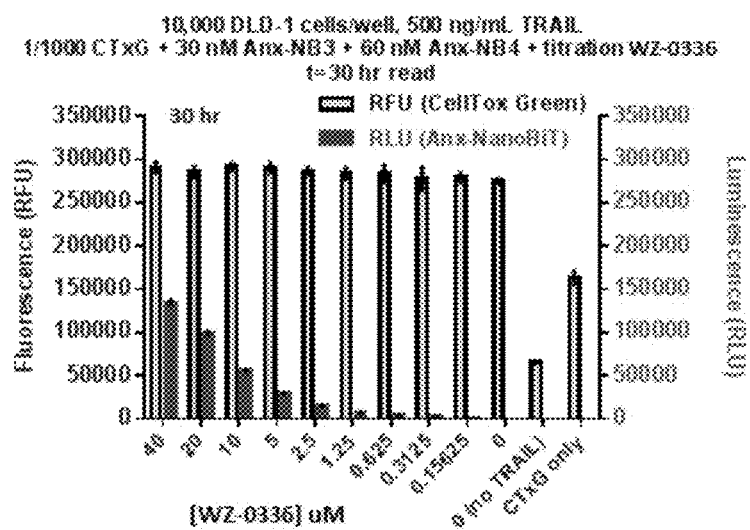

The disclosed serum stable compounds also exhibit tunable reactivity, tunable signal strength, and tunable assay windows, which depend on the concentration and the needs of an assay. For example, the compounds WZ-0451 and WZ-0420 exhibit a stable signal within 15 hours when concentration is above 20 uM, and the strength of signal is 10 times brighter than the traditional pro-substrate PBI-4377 (FIG. 3I and FIG. 3K). However, the other disclosed compounds WZ-0416 and WZ-0461 exhibit stable signal over 24 hours in a manner of less dependent on the concentration, but with decreased brightness, which is comparable or slightly better than compound PBI-4377 (FIG. 3J, FIG. 3L, FIG. 5C and FIG. 5D). In contrast, the serum instable compounds, WZ-0308, WZ-0429. WZ-0439, WZ-0454, and WZ-0441 (FIG. 1A-FIG. 1H), showed rapid signal decay almost independent of concentration (FIG. 3A, FIG. 3E-FIG. 3H). Therefore, the disclosed serum stable pro-substrates are capable of maintaining a sustainable luminescent signal over a desired incubation time window, which may or may not fully rely on the esterase activity inside a cell, and which also may be contrary to the traditional expectations that an assay window and/or signal may solely depend on the esterase activity a inside cell.

In addition to the superior serum stability of the present compounds, in some embodiments, bioluminescent live cell assays could be improved by improving the compounds' solubility and/or cell permeability. In some embodiments, the present compounds contain polyethylene glycol (PEG) moieties with various numbers of repeating units. The length of the PEG moieties may improve cell permeability and solubility of the present compounds in live cell assays. The PEG moieties and other protection groups of the present compounds may be cleaved by a deprotection enzyme (such as an esterase) in a live cell assay to release a luciferase substrate (such as furimazine). As a non-limiting example, a comparison of three different pro-furimazine esters, WZ-0308, PBI-4377, and disclosed compound WZ-0324, was conducted using 10 ng/well of CMV promoter-Nano-Luc® gene transfected into HEK293 cells in DMEM media in the presence of 10% FBS with/without adding exogenous esterase porcine liver esterase (PLE). The results show that the serum instable compound WZ-0308 released furimazine rapidly in the presence of FBS, but the luminescent signal was not sustainable over long period of time even without the addition of exogenous PLE (FIG. 3A, rapid signal decay during the first 2-3 hours). On the other hand, both the traditional live cell pro-substrate PBI-4377 and disclosed compound WZ-0324 exhibited a stable signal over 24 hours or beyond in the absence of exogenous PLE esterase (FIGS. 3B and 3C). The luminescent signals for PBI-4377 and WZ-0324 were comparable and were both significantly enhanced by the additional of exogenous esterase (FIGS. 3B and 3C). The results also suggest that WZ-0324 may have decreased esterase activity than PBI-4377 since the signal observed for PBI-4377 following PLE addition (FIG. 3B) was generally higher than that of WZ-0324 (FIG. 3C). Further, the results suggest that WZ-0324 may have higher cell permeability than PBI-4377 (FIGS. 3B and 3C, higher signal of WZ-0324 in the absence of exogenous PLE esterase). The results suggest that WZ-0324 may have an enhanced solubility than PBI-4377 (haze observed for PBI-4377 at above 50 μM vs. WZ-0324 at above 70 μM). The solubility or cell permeability can be further enhanced by increasing the length of PEGs or incorporating other water soluble groups, such as amino groups or hydroxyl groups, which may further improve live cell assay performance without the need to add exogenous esterase.

"Biocompatibility" refers to the tolerance of a cell (e.g., prokaryotic or eukaryotic) to a pro-coelenterazine or pro-furimazine compound (e.g., compounds of formula (I)). Biocompatibility of a pro-coelenterazine or pro-furimazine compound is related to the stress it causes on the host cell. The slow release of active furimazine or coelenterazine from a pro-coelenterazine or pro-furimazine compound (e.g., compounds of formula (I)) may, in some embodiments, reduce or eliminate the toxicity caused by active molecule itself and improve the tolerance of the cell to such compounds.

Enhanced biocompatibility of the pro-coelenterazine analogue (e.g., compounds of formula (I), formula (II) and formula (III)), may be determined by measuring cell viability and/or growth rate of cells. For example, enhanced biocompatibility of the pro-coelenterazine analogues may be determined by measuring cell viability in the absence of luciferase expression of cells exposed to the pro-coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® technology), or another method known in the art. The effect of the disclosed compounds on cell viability or apoptosis may be compared to the effect of native or known coelenterazine analogues on cell viability or apoptosis.

Enhanced biocompatibility may also be determined by measuring the effect of the disclosed compounds (e.g., compounds of formula (I), formula (II) and formula (III)) on cell growth or gene expression. For example, enhanced biocompatibility of the compounds of formula (I), formula (II), or formula (III) may be determined by measuring the cell number after a period of time or by determining the expression of stress response genes in a sample of cells that are exposed to compounds of formula (I), formula (II), or formula (III) compared to cells exposed to a native or known coelenterazine analogue or no coelenterazine. The effect of the disclosed compounds on cell growth or gene expression may be compared to a native or known coelenterazine analogue.

B. Synthesis Methods

Compounds of formula (I), formula (II) and formula (III), and other furimazine-O-methyl carboxyl esters can be synthesized as shown in Schemes 2a and Scheme 2b.

Scheme 2a. Synthesis of furimazine-O-methyl Me-PEG$_n$-OCH$_2$-dimethylpropanoates WZ-0323, WZ-0333, WZ-0324, WZ-0336 and WZ-0364, and furimazine-O-methyl Me-PEG$_n$-OCH$_2$-propanoates WZ-0308, WZ-0310 and WZ-0315.

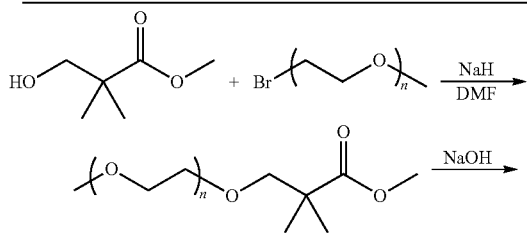

1a: n = 1, 33%
2a: n = 2, 22%
3a: n = 3, 32%
4a: n = 4, 71%

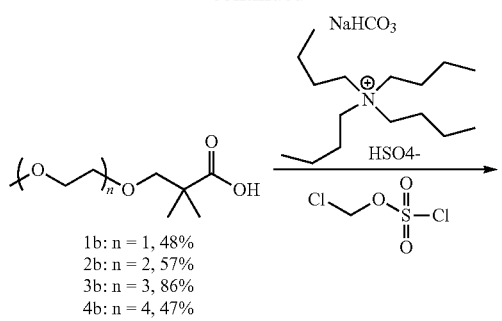

1b: n = 1, 48%
2b: n = 2, 57%
3b: n = 3, 86%
4b: n = 4, 47%

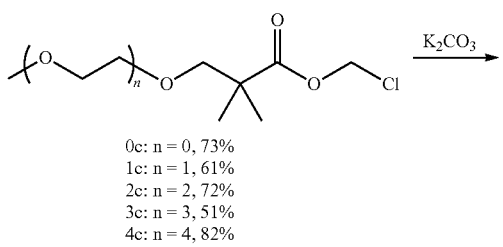

0c: n = 0, 73%
1c: n = 1, 61%
2c: n = 2, 72%
3c: n = 3, 51%
4c: n = 4, 82%

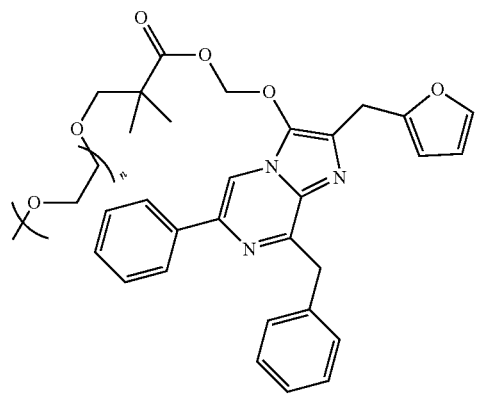

WZ-0323: n = 0, 33%
WZ-0333: n = 1, 27%
WZ-0324: n = 2, 16%
WZ-0336: n = 3, 23%
WZ-0364: n = 4, 20%

Scheme 2b. Synthesis of pro-furimazines WZ-0451, WZ-0467, WZ-0420, WZ-0461, WZ-0416, WZ-0419, WZ-0415, WZ-0429, WZ-0439, WZ-0454, WZ-0441, WZ-0440 and WZ-0430.

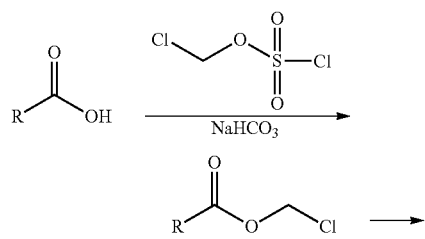

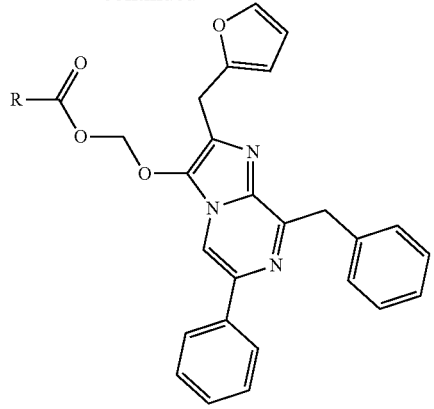

As shown in Scheme 2a, furimazine-O-methyl Me-PEG$_n$-OCH$_2$-dimethylpropanoates WZ-0323, WZ-0333, WZ-0324, WZ-0336, and WZ-0364 can be synthesized by employing a similar method. In one embodiment, compounds WZ-0333, WZ-0324, WZ-0336, and WZ-0364 were prepared by a four-step synthesis with the exception of compound WZ-0323 due to the commercial availability of 3-methoxy-2,2-dimethylpropanoic acid. Methyl 3-hydroxy-2,2-dimethylpropanoate was deprotonated with sodium hydride in dry DMF at 0° C. and then reacted with bromo-PEG$_{1-4}$-Me ether compounds to generate methyl Me-PEG$_{1-4}$-dimethyl propionates (1a-4a). Compounds 1a-4a were then hydrolyzed under basic conditions at 65° C. to produce the corresponding acids. The acids 1b-4b reacted with chloromethyl chlorosulfonate under slightly basic conditions in the presence of n-tetrabutyl ammonium hydrogen sulfate at 0° C. and yielded the intermediates chloromethyl Me-PEGn-dimethyl propionates 1c-4c. Furimazine was alkylated with compound 0c-4c to give the final target molecules WZ-0323, WZ-0333, WZ-0324, WZ-0336, and WZ-0364. Similarly, pro-furimazines WZ-0451, WZ-0451, WZ-0467, WZ-0420, WZ-0461, WZ-0416, WZ-0419, WZ-0415, WZ-0429, WZ-0439, WZ-0454, WZ-0441, WZ-0440, and WZ-0430 can be synthesized by employing the above mentioned method by converting acids to their chloromethyl esters followed by subsequent alkylation of furimazine.

Reaction conditions and reaction times for each individual step may vary depending on the particular reactants employed and substituents present in the reactants used.

Non-limiting examples of procedures for preparing the present compounds are provided in the Examples section. Reactions may be worked up in the conventional manner, e.g., by eliminating the solvent from the residue and further purified according to methodologies generally known in the art, including but not limited to, crystallization, distillation, extraction, trituration, and chromatography. The starting materials and reagents may be either commercially available or prepared from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. METHODS OF USE AND KITS

The present compounds may be used in any way that luciferase substrates, e.g., coelenterazine analogues, have been used. In particular, the present compound may be used in live cell assays, including reporter assay, NanoBiT™ assay and NanoBRET™ assay, Annexin assay, etc. When a stable pro-coelenterazine or pro-furimazine is used in live cell assays, the accuracy of the assays is greatly increased because of the reduction of light produced by destabilization of the luminophore.

The present compounds may be used in a method for detecting luminescence in a sample, the method comprising: contacting a sample with a compound disclosed herein; contacting the sample with a deprotection enzyme, if no deprotection enzyme is present in the sample; contacting the sample with a coelenterazine-utilizing luciferase, if no coelenterazine-utilizing luciferase is present in the sample; and detecting luminescence.

The deprotection enzyme as used herein refers to enzymes that are capable of converting pro-coelenterazine or pro-furimazine compounds to the luminophore compounds furimazine or coelenterazine. Various deprotection enzymes may be used as deprotection enzymes. In some embodiments, the deprotection enzymes include, but are not limited to, esterase.

In certain embodiments, the sample comprises live cells. The live cells may include those from an animal (e.g., a vertebrate), a plant, a fungus, physiological fluid (e.g., blood, plasma, urine, mucous secretions), or cell culture.

In certain embodiments, the sample comprises a coelenterazine-utilizing luciferase or a fragment complementary luciferase.

In certain embodiments, the pro-coelenterazines or pro-furimazines may be used as assay reagents. Assays using luciferases are well known in the art. Such assays are particularly useful for analyzing biological mechanisms, such as gene expression and regulation in live cells. Typically, cells are transfected with a nucleic acid encoding a luciferase, and the presence of luciferase is determined by the addition of reagents with cells, including the pro-coelenterazine analogue. The pro-coelenterazine can be deprotected by the enzyme present in cells to release luminophore.

In some embodiments, a pro-coelenterazine or pro-furimazine is used in a live cell assay comprising NanoLuc® luciferase or *Renilla* luciferase. NanoLuc® or *Renilla* luciferase may be the sole light producing protein in the assay, and esterases present in live cells may be the deprotection enzyme.

In some embodiments, a pro-coelenterazine or pro-furimazine is used in live cell assays comprising protein-NanoLuc® fragment complementary assays for reporter gene expression and regulation in live cells.

In some embodiments, a pro-coelenterazine or pro-furimazine is used in live cell assays comprising protein of interests fused with NanoLuc® fragments for NanoLuc® complementary assays to investigate protein-protein interaction.

In some embodiments, a pro-coelenterazine or pro-furimazine is used in a real time assay comprising Annexin-complementary NanoLuc® fragments for a real time apoptosis assay. Annexins are a family of calcium-dependent phospholipid-binding proteins. In healthy cells, phosphatidylserine is predominantly located along the cytosolic side of the plasma membrane. Phosphatidyl serine actively translocates to the extracellular membrane as a result of the induction of apoptosis. This early biomarker of the apoptotic cascade can be measured by Nanoluc complementary fragment-fused Annexin V proteins which bind to phosphatidylserine and can react with furimazine or coelenterazine to detect apoptotic cells by luminescence.

In some embodiments, a pro-coelenterazine or pro-furimazine is used in live cell bioluminescence resonance energy transfer (BRET) assay. BRET can be determined if two molecules are capable of binding each other or are co-localized in a cell. BRET involves the use of either two bioluminescent molecules or one bioluminescent molecule and one fluorescent molecule. The molecules are chosen such that the emission wavelength of the donor is within the excitation spectra of the acceptor. Furthermore, the excitation and emission spectra of the two molecules should overlap minimally if at all. When the molecules are in close proximity to each other, excitation of the donor leads to a transfer of the energy to the acceptor rather than an emission of light. The acceptor then emits the transferred energy as light. Thus, when the molecules are in close proximity to each other, light detected from the donor is low, while light detected from the acceptor is high. When the molecules are not in close proximity to each other, light detected from the donor is high, while light detected from the acceptor is low. By linking the donor to a first protein and the acceptor to a second protein, interaction of the two proteins can be determined by the detection of BRET. In preferred embodiments, the donor is Nanoluc luciferase and the acceptor is red fluorescence dyes.

In some embodiments, a pro-coelenterazine or pro-furimazine is used in an assay wherein a deprotection enzyme can be added as exogenous enzyme along with the addition of the assay reagents. Such assays may be useful in methods of releasing the active luminophore (e.g. coelenterazine or furimazine) rapidly in a sample for certain live cell assays that require reaching the maximal brightness over a short time period but still require maintaining a reasonably stable signal over a certain time period.

In certain embodiments, the compounds of formula (I), formula (II), and formula (III) is not limited to in vitro or in situ live cell environments, but can be extended to in vivo studies. Applications of the pro-coelenterazine or pro-furimazine to in vivo luminescent analysis will be readily apparent to those skilled in the art.

In the embodiments wherein a luciferase, protein-fused luciferase or fragment complementary luciferase is expressed in cells, the cells are treated with pro-furimazine or pro-coelenterazine analogues (e.g., a compound of formula (I), formula (II) and formula (III)), the pro-substrates will permeate cells in culture to release furimazine or coelenterazine, and then react with the luciferase, protein-fused luciferase, or complementary luciferase and generate luminescence. Enhancement of cell permeability for the pro-substrate by chemical modification may improve assay performance.

In the embodiments wherein live cell assays are needed, fetal bovine serum (FBS) might be necessary component to maintain cell health in media or culture. The compounds of formula (I), by virtue of their increased stability in media containing FBS, may be used for more robust, live cell luciferase-based assays.

In still other embodiments, a sample (including cells, tissues, animals, etc.) containing a luciferase or fragment complimentary luciferase and a compound of formula (I), formula (II), and formula (III) may be assayed using various microscopy and imaging techniques, e.g., in vivo imaging.

In still other embodiments, a secretable luciferase is expressed in cells as part of a live-cell assay system.

In addition to being cell permeant, the compounds of formula (I), formula (II), and formula (III) may show comparable biocompatibility to native coelenterazine in terms of cell viability.

In certain embodiments, the present compounds can be used in a method for detecting luminescence in a transgenic animal. The method comprises administering a compound of the present compounds to a transgenic animal expressing a coelenterazine-utilizing luciferase, and detecting luminescence.

In certain embodiments, the compounds of formula (I), formula (II), and formula (III) disclosed herein may be provided as part of a kit. The kit may include one or more luciferases (in the form of a polypeptide, a polynucleotide, or both) and a pro-furimazine or pro-coelenterazine analogue of formula (I), formula (II), and formula (III) along with suitable reagents and instructions to enable a user to perform assays such as those disclosed herein. The kit may also include one or more buffers such as those disclosed herein.

4. EXAMPLES

Example 1: Synthesis of Furimazine methyl Me-PEG$_0$-OCH$_2$-dimethylpropanoate (WZ-0323)

Synthesis of Me-PEG$_0$-OCH$_2$-Dimethyl-COOCH$_2$Cl (0c)

Me-PEG$_0$-OCH$_2$-dimethylpropanoic acid (1.0 g, 7.57 mmol) was diluted in a 20 mL/20 mL mixture of dichloromethane/water. The mixture was cooled in an ice-water bath, and sodium bicarbonate (2.54 g, 30.27 mmol, 4 equiv) and n-tetrabutyl ammonium hydrogen sulfate (0.128 g, 0.378 mmol, 0.05 equiv) was added. After stirring for 5 min, chloromethyl chlorosulfonate (1.37 g, 8.32 mmol, 1.1 equiv) was added at 0° C. The solution was stirred vigorously overnight. The mixture was transferred to a separation funnel with more dichloromethane and washed with saturated sodium chloride solution. The organic layers were dried over sodium sulfate. Removal of solvent generated the crude product in a yield of 73.2% (1.37 g). The compound was used directly in next step without further purification.

((8-benzyl-2-(furan-2-ylmethyl)-6-phenylimidazo[1,2-a]pyrazin-3-yl)oxy)methyl 3-methoxy-2,2-dimethylpropanoate (WZ-0323)

The mixture of Me-PEG$_0$-OCH$_2$-Dimethyl-COOCH$_2$Cl (0c) (0.378 g, 2.10 mmol) and KI (0.348 g, 2.10 mmol) in 5 ml DMF was stirred for 30 minutes under argon. Furimazine (0.20 g, 0.524 mmol) and K$_2$CO$_3$ (0.290 g, 2.10 mmol) were added, and the resulting mixture was stirred for another 30 minutes. The mixture was diluted with 20 mL of DCM and washed with water and brine. The organic layer was dried over Na$_2$SO$_4$. The compound was purified by ESCO flash chromatography using heptane/ethyl acetate as eluent to yield the desired product (90 mg, 33%). $^1$HNMR (d6-DMSO, δ ppm): 8.52 (s, 1H), 8.00-8.20 (m, 2H), 7.40-7.70 (m, 6H), 7.20-7.38 (m, 3H), 6.48 (d, 1H), 6.21 (d, 1H), 5.74 (s, 2H, —OCH$_2$O—), 4.49 (s, 2H, —CH$_2$), 4.18 (s, 2H, —CH$_2$), 3.33 (s, 2H, —OCH$_2$), 3.01 (s, 3H, —OCH$_3$), 1.0 (s, 6H, CH$_3$). MS (m/e) (C$_{31}$H$_{31}$N$_3$O$_5$) calculated 525.23, observed 526.2[M+H]; HPLC purity 100% at 260 nm.

Example 2: Synthesis of Furimazine-O-methyl Me-PEG$_1$-OCH$_2$-dimethylpropanoate (WZ-0333)

Synthesis of Methyl Me-PEG$_1$-OCH$_2$-dimethylpropanoate (1a)

Sodium hydride (60% wt in oil) (6.28 g, mmol) was added to a stirred solution of methyl 3-hydroxy-2,2-dimethylpropanoate (10.40 g, 78.69 mmol) in DMF 20 ml at 0° C., after 5 min 1-bromo-2-methoxyethane (10.94 g, 78.69 mmol) was added dropwise, and the reaction mixture was allowed to stir for 3 h. The reaction was quenched with cold saturated NH$_4$Cl (aq.) (30 mL), the aqueous layer extracted with DCM (2×50 mL), and the combined organic layers dried over Na$_2$SO$_4$. After removing the solvent, the compound was purified by ESCO flash chromatography using heptane/ethyl acetate as eluent to yield 33% of product (5.0 g).

Synthesis of Me-PEG$_1$-OCH$_2$-dimethylpropanic acid (1b)

A suspension of methyl Me-PEG$_1$-OCH$_2$-dimethylpropanoate (5.0 g, 0.0284 mmol) in 2 M KOH in water (60 mL) was stirred at 65° C. for 7 hours. The aqueous layer was washed with DCM (3×30 mL), acidified to pH 1-2 with 6 M HCl (aq.), and extracted with DCM (3×30 mL). The combined organics were dried (Na$_2$SO$_4$), filtered, and concentrated under vacuum to afford the desired product as a light yellow oil (2.42 g, 48%).

Synthesis of Chloromethyl Me-PEG$_1$-OCH$_2$-dimethylpropanoate (1c)

Me-PEG$_1$-OCH$_2$-dimethyl-propanic acid (2.42 g, 13.73 mmol) was diluted in a 20 mL/20 mL mixture of dichloromethane/water. The mixture was cooled in an ice-water bath, and sodium bicarbonate (4.61 g, 54.93 mmol, 4 equiv) and n-tetrabutyl ammonium hydrogen sulfate (0.233 g, 0.687 mmol, 0.05 equiv) was added. After stirring for 5 min, chloromethyl chlorosulfonate (2.49 g, 15.11 mmol, 1.1 equiv) was added at 0° C. The solution was stirred vigorously overnight. The mixture was transferred to a separation funnel with more dichloromethane and washed with saturated sodium chloride solution. The organic layers were dried over sodium sulfate. Removal of solvent generated the crude product in a yield of 60.9% (1.88 g). The compound was used directly in the next step without further purification.

Synthesis of ((8-benzyl-2-(furan-2-ylmethyl)-6-phenylimidazo[1,2-a]pyrazin 3-yl)oxy)methyl 3-(2-methoxyethoxy)-2,2-dimethylpropanoate (WZ-0333)

The mixture of chloromethyl Me-PEG$_1$-OCH$_2$-dimethylpropranoate (1c) (0.53 g, 2.36 mmol) and KI (0.391 g, 2.36 mmol) in 5 mL DMF was stirred for 30 minutes under argon. Furimazine (0.30 g, 0.786 mmol) and K$_2$CO$_3$ (0.435 g, 3.15 mmol) were added, and the resulting mixture was stirred for another 30 minutes. The mixture was diluted with 20 ml of DCM and washed with water and brine. The organic layer was dried over Na$_2$SO$_4$. The compound was purified by ESCO flash chromatography using heptane/ethyl acetate as eluent to yield the desired product (120 mg, 27%). $^1$HNMR (d6-DMSO, δ ppm): 8.59 (s, 1H), 8.10-8.30 (m, 2H), 7.30-7.70 (m, 6H), 7.20-7.35 (m, 3H), 6.46 (d, 1H), 6.21 (d, 1H), 5.75 (s, 2H, —OCH$_2$O—), 4.38 (s, 2H, —CH$_2$), 4.15 (s, 2H, —CH$_2$), 3.20-3.40 (m, 6H), 3.08 (s, 3H, —OCH$_3$), 1.0 (s, 6H, CH$_3$). MS (m/e) (C$_{33}$H$_{35}$N$_3$O$_6$) calculated 569.25 [M+H], observed 570.2; HPLC purity 92.5% at 260 nm.

Compounds WZ-0324, WZ-0336 WZ-0364, WZ-0451, WZ-0467, WZ-0420, WZ-0461, WZ-0416, WZ-0419, WZ-0415, WZ-0429, WZ-0439, WZ-0454, WZ-0441, WZ-0440 and WZ-0430 were synthesized using methods similar to that employed for the synthesis of WZ-0333.

((8-benzyl-2-(furan-2-ylmethyl)-6-phenylimidazo[1,2-a]pyrazin-3-yl)oxy)methyl 3-(2-(2-methoxyethoxy)ethoxy)-2,2-dimethylpropanoate (WZ-0324)

$^1$HNMR (d6-DMSO, δ ppm): 8.62 (s, 1H), 8.00-8.20 (m, 2H), 7.30-7.65 (m, 6H), 7.10-7.30 (m, 3H), 6.38 (d, 1H), 6.19 (d, 1H), 5.78 (s, 2H, —OCH$_2$O—), 4.45 (s, 2H, —CH$_2$), 4.19 (s, 2H, —CH$_2$), 3.25-3.50 (m, 10H), 3.12 (s, 3H, —OCH$_3$), 1.01 (s, 6H, CH$_3$). MS (m/e) (C$_{35}$H$_{39}$N$_3$O$_7$) calculated 613.28, observed 614.2 [M+H]; HPLC purity 100% at 260 nm.

((8-benzyl-2-(furan-2-ylmethyl)-6-phenylimidazo[1,2-a]pyrazin-3-yl)oxy)methyl 13,13-dimethyl-2,5,8,11-tetraoxatetradecan-14-oate (WZ-0336)

$^1$HNMR (d6-DMSO, δ ppm): 8.57 (s, 1H), 8.0-8.25 (m, 2H), 7.30-7.65 (m, 6H), 7.20-7.30 (m, 3H), 6.42 (d, 1H), 6.22 (d, 1H), 5.75 (s, 2H, —OCH$_2$O—), 4.43 (s, 2H, —CH$_2$), 4.20 (s, 2H, —CH$_2$), 3.20-3.50 (m, 14H), 3.11 (s, 3H, —OCH$_3$), 1.0 (s, 6H, CH$_3$). MS (m/e) (C$_{37}$H$_{43}$N$_3$O$_8$) calculated 657.31, observed 658.3 [M+H]; HPLC purity 99.6% at 260 nm.

((8-benzyl-2-(furan-2-ylmethyl)-6-phenylimidazo[1,2-a]pyrazin-3-yl)oxy)methyl 16,16-dimethyl-2,5,8,11,14-pentaoxaheptadecan-17-oate (WZ-0364)

$^1$HNMR (d$_6$-DMSO, δ ppm): 8.59 (s, 1H), 8.0-8.2 (m, 2H), 7.30-7.60 (m, 6H), 7.20-7.30 (m, 3H), 6.39 (d, 1H), 6.18 (d, 1H), 5.79 (s, 2H, —OCH$_2$O—), 4.42 (s, 2H, —CH$_2$), 4.19 (s, 2H, —CH$_2$), 3.22-3.55 (m, 18H), 3.17 (s, 3H, —OCH$_3$), 1.0 (s, 6H, CH$_3$). MS (m/e) [M+H] (C$_{39}$H$_{47}$N$_3$O$_9$) calculated 701.33, observed 702.3 [M+H]; HPLC purity 100% at 260 nm.

((8-benzyl-2-(furan-2-ylmethyl)-6-phenylimidazo[1,2-a]pyrazin-3-yl)oxy)methyl 2-methoxy-2-methylpropanoate (WZ-0451)

$^1$HNMR (d$_6$-DMSO, δ ppm): 8.63 (s, 1H), 8.0-8.2 (m, 2H), 7.35-7.60 (m, 6H), 7.15-7.35 (m, 3H), 6.37 (d, 1H), 6.19 (d, 1H), 5.85 (s, 2H, —OCH$_2$O—), 4.50 (s, 2H, —CH$_2$), 4.21 (s, 2H, —CH$_2$), 3.00 (s, 3H, —OCH$_3$), 1.25 (s, 6H, CH$_3$). MS (m/e) (C$_{30}$H$_{29}$N$_3$O$_5$) calculated 511.21, observed 512.2 [M+H]; HPLC purity 98% at 260 nm.

((8-benzyl-2-(furan-2-ylmethyl)-6-phenylimidazo[1,2-a]pyrazin-3-yl)oxy)methyl 2-acetamido-2-methylpropanoate (WZ-0467)

$^1$HNMR (d$_6$-DMSO, β ppm): 8.70 (s, 1H), 8.38 (s, 1H, NH), 8.0-8.2 (m, 2H), 7.30-7.65 (m, 6H), 7.15-7.35 (m, 3H), 6.38 (d, 1H), 6.22 (d, 1H), 5.76 (s, 2H, —OCH$_2$O—), 4.49 (s, 2H, —CH$_2$), 4.23 (s, 2H, —CH$_2$), 1.74 (s, 3H, CH$_3$C=O), 1.25 (s, 6H, CH$_3$). MS (m/e) C$_{31}$H$_{30}$N$_4$O$_5$ calculated 538.22, observed 539.2 [M+H]; HPLC purity 99% at 260 nm.

((8-benzyl-2-(furan-2-ylmethyl)-6-phenylimidazo[1,2-a]pyrazin-3-yl)oxy)methyl furan-2-carboxylate (WZ-0420)

$^1$HNMR (d$_6$-DMSO, δ ppm): 8.60 (s, 1H), 7.85-8.05 (m, 3H), 7.1-7.6 (m, 10H), 6.61 (d, 1H), 6.36 (d, 1H), 6.18 (d, 1H), 5.93 (s, 2H, —OCH$_2$O—), 4.43 (s, 2H, —CH$_2$), 4.13 (s, 2H, —CH$_2$). MS (m/e) C$_{30}$H$_{23}$N$_3$O$_5$ calculated 505.16, observed 506.2 [M+H]; HPLC purity 90% at 260 nm.

((8-benzyl-2-(furan-2-ylmethyl)-6-phenylimidazo[1,2-a]pyrazin-3-yl)oxy)methyl furan-3-carboxylate (WZ-0461)

$^1$HNMR (d$_6$-DMSO, δ ppm): 8.73 (s, 1H), 8.41 (s, br, 1H), 7.85-8.05 (m, 2H), 7.80 (d, 1H), 7.3-7.6 (m, 6H), 7.2-7.3 (m, 3H), 6.76 (d, 1H), 6.33 (d, 1H), 6.14 (d, 1H), 5.96 (s, 2H, —OCH$_2$O—), 4.49 (s, 2H, —CH$_2$), 4.14 (s, 2H, —CH$_2$). MS (m/e) C$_{30}$H$_{23}$N$_3$O$_5$ calculated 505.16, observed 506.3 [M+H]; HPLC purity 98.8% at 260 nm.

((8-benzyl-2-(furan-2-ylmethyl)-6-phenylimidazo[1,2-a]pyrazin-3-yl)oxy)methyl benzoate (WZ-0416)

$^1$HNMR (d$_6$-DMSO, δ ppm): 8.59 (s, 1H), 7.8-8.0 (m, 4H), 7.6-7.7 (m, 1H), 7.3-7.5 (m, 8H), 7.1-7.3 (m, 3H), 6.38 (d, 1H), 6.14 (d, 1H), 6.0 (s, 2H, —OCH$_2$O—), 4.42 (s, 2H, —CH$_2$), 4.11 (s, 2H, —CH$_2$). MS (m/e) C$_{32}$H$_{25}$N$_3$O$_5$ calculated 515.18, observed 516.2 [M+H]; HPLC purity 99.8% at 260 nm.

((8-benzyl-2-(furan-2-ylmethyl)-6-phenylimidazo[1,2-a]pyrazin-3-yl)oxy)methyl methyl carbonate (WZ-0419)

$^1$HNMR (d$_6$-DMSO, δ ppm): 8.61 (s, 1H), 7.9-8.1 (m, 2H), 7.3-7.6 (m, 6H), 7.1-7.3 (m, 3H), 6.38 (d, 1H), 6.17 (d, 1H), 5.78 (s, 2H, —OCH$_2$O—), 4.47 (s, 2H, —CH$_2$), 4.16 (s, 2H, —CH$_2$), 3.71 (s, 3H, OCH$_3$). MS (m/e) C$_{27}$H$_{23}$N$_3$O$_5$ calculated 469.16, observed 470.2 [M+H]; HPLC purity 97.8% at 260 nm.

The following compounds were prepared using the general procedure of Scheme 2a and Scheme 2b.

| compound | Structure | Yield (%) | MS [M + H] |
|---|---|---|---|
| WZ-0323 | 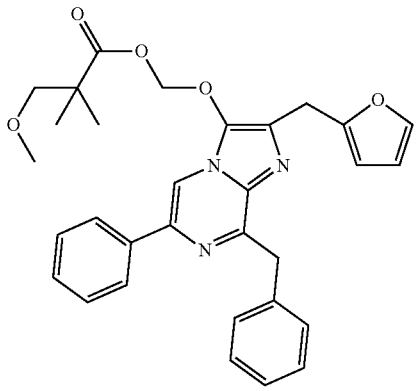 [SMILES: COCC(C)(C)C(=O)OCOc1c(Cc2ccco2)nc2c(Cc3ccccc3)nc(-c3ccccc3)cn12] ((8-benzyl-2-(furan-2-ylmethyl)-6-phenylimidazo[1,2-α]pyrazin-3-yl)oxy)methyl 3-methoxy-2,2-dimethylpropanoate | 33% | 526.2 |
| WZ-0324 | 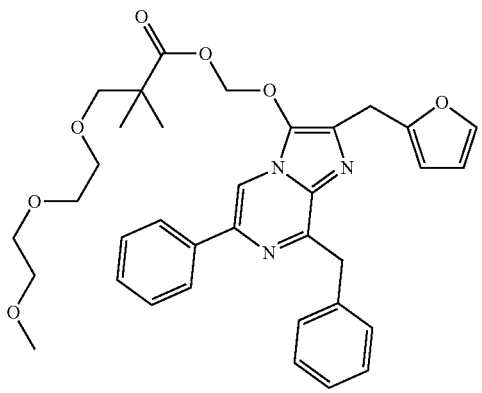 [SMILES: COCCOCCOCC(C)(C)C(=O)OCOc1c(Cc2ccco2)nc2c(Cc3ccccc3)nc(-c3ccccc3)cn12] ((8-benzyl-2-(furan-2-ylmethyl)-6-phenylimidazo[1,2-α]pyrazin-3-yl)oxy)methyl 3-(2-(2-methoxyethoxy)ethoxy)-2,2-dimethylpropanoate | 16% | 614.2 |

| compound | Structure | Yield (%) | MS [M + H] |
|---|---|---|---|
| WZ-0333 | 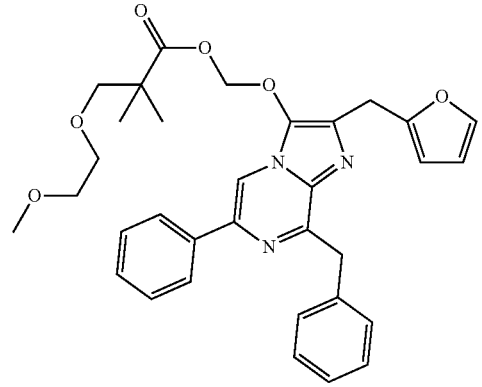 [SMILES: COCCOCC(C)(C)C(=O)OCOc1c(Cc2ccco2)nc2c(Cc3ccccc3)nc(-c3ccccc3)cn12] ((8-benzyl-2-(furan-2-ylmethyl)-6-phenylimidazo[1,2-α]pyrazin-3-yl)oxy)methyl 3-(2-methoxyethoxy)-2,2-dimethylpropanoate | 27% | 570.2 |
| WZ-0336 | 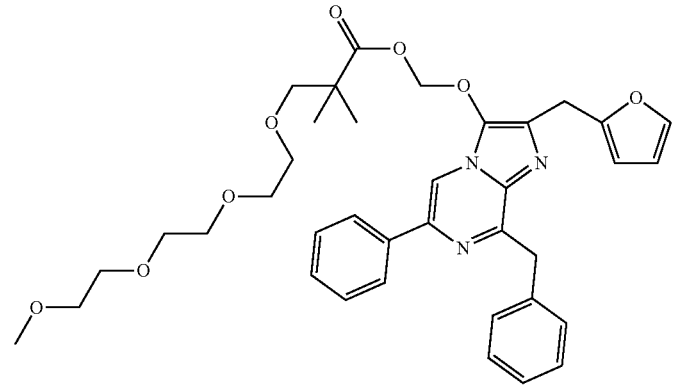 [SMILES: COCCOCCOCCOCC(C)(C)C(=O)OCOc1c(Cc2ccco2)nc2c(Cc3ccccc3)nc(-c3ccccc3)cn12] ((8-benzyl-2-(furan-2-ylmethyl)-6-phenylimidazo[1,2-α]pyrazin-3-yl)oxy)methyl 13,13-dimethyl-2,5,8,11-tetraoxatetradecan-14-oate | 23% | 658.3 |
| WZ-0364 | 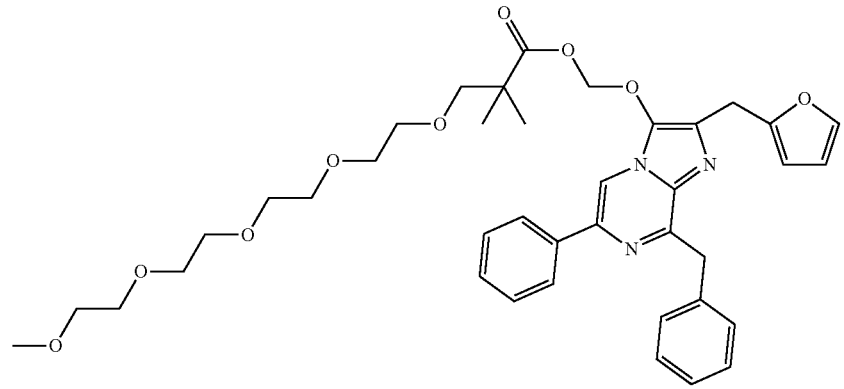 [SMILES: COCCOCCOCCOCCOCC(C)(C)C(=O)OCOc1c(Cc2ccco2)nc2c(Cc3ccccc3)nc(-c3ccccc3)cn12] ((8-benzyl-2-(furan-2-ylmethyl)-6-phenylimidazo[1,2-a]pyrazin-3-yl)oxy)methyl 16,16-dimethyl-2,5,8,11,14-pentaoxaheptadecan-17-oate | 20% | 702.3 |

-continued

| compound | Structure | Yield (%) | MS [M + H] |
|---|---|---|---|
| WZ-0451 | ((8-benzyl-2-(furan-2-ylmethyl)-6-phenylimidazo[1,2-a]pyrazin-3-yl)oxy)methyl 2-methoxy-2-methylpropanoate | 25% | 512.2 |
| WZ-0467 | ((8-benzyl-2-(furan-2-ylmethyl)-6-phenylimidazo[1,2-a]pyrazin-3-yl)oxy)methyl 2-acetamido-2-methylpropanoate | 25% | 539.2 |
| WZ-0420 | ((8-benzyl-2-(furan-2-ylmethyl)-6-phenylimidazo[1,2-a]pyrazin-3-yl)oxy)methyl furan-2-carboxylate | 22% | 506.2 |

-continued
| compound | Structure | Yield (%) | MS [M + H] |
|---|---|---|---|
| WZ-0461 | 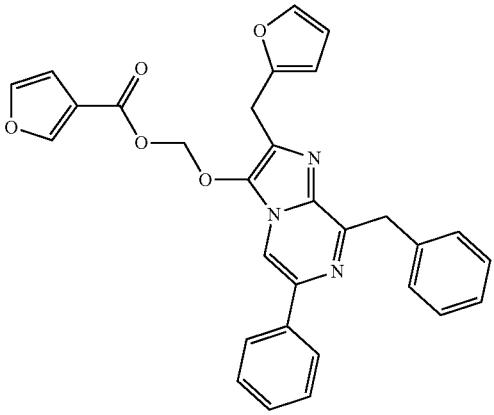 [SMILES: O=C(OCOc1c(Cc2ccco2)nc2c(Cc3ccccc3)nc(-c3ccccc3)cn12)c1ccoc1]<br>((8-benzyl-2-(furan-2-ylmethyl)-6-phenylimidazo[1,2-a]pyrazin-3-yl)oxy)methyl furan-3-carboxylate | 34% | 506.3 |
| WZ-0416 | 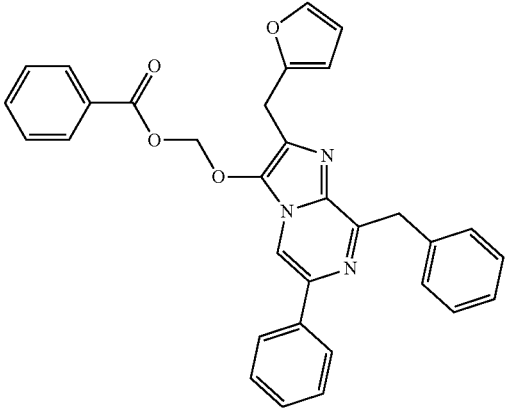 [SMILES: O=C(OCOc1c(Cc2ccco2)nc2c(Cc3ccccc3)nc(-c3ccccc3)cn12)c1ccccc1]<br>((8-benzyl-2-(furan-2-ylmethyl)-6-phenylimidazo[1,2-a]pyrazin-3-yl)oxy)methyl benzoate | 38% | 516.2 |
| WZ-0419 | 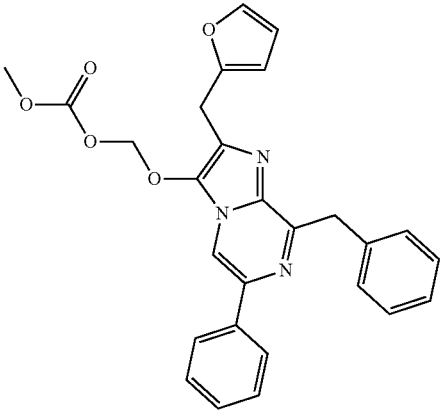 [SMILES: COC(=O)OCOc1c(Cc2ccco2)nc2c(Cc3ccccc3)nc(-c3ccccc3)cn12]<br>((8-benzyl-2-(furan-2-ylmethyl)-6-phenylimidazo[1,2-a]pyrazin-3-yl)oxy)methyl methyl carbonate | 37% | 470.2 |

Example 3: General Protocol of Stability Tests for Pro-Furimazines or Pro-Coelenterazines in DMSO or Media with or without Fetal Bovine Serum The tested compounds were dissolved in DMSO stock at a concentration of 20 mM. The stock solution was further diluted to 40 μM in DMSO control or DMEM media with/without FBS. Three 40 uM dilutions of each compound were measured by HPLC using specific elution solvent/buffer (e.g. 0.1% TFA and acetonitrile) under the same conditions over 24 hours. The percentage of purity at certain time points was calculated by the peak area of the tested compound divided by the total peak areas of all the compounds including the tested compound and degradation compounds at their corresponding retention time at 260 nm. The changes of purity of the tested compound over time indicated the degree of instability of the compound in a specific environment with/without 10% of FBS. FIGS. 1A-1H show that compounds WZ-0308, WZ-0310, WZ-0315, WZ-0429, WZ-0454, WZ-0439 and WZ-0441 demonstrated poor serum stability, with approximately 50% or more degradation in DMEM media with 10% FBS after 5 hours. WZ-0415 showed an enhanced serum stability with approximately 50% degradation with 10% FBS after 10 hours. In comparison, compounds WZ-0323, WZ-0324, WZ-0336, WZ-0451, WZ-0467, WZ-0420, WZ-0461, WZ-0416, and WZ-0419 demonstrated improved serum stability, with <20% degraded in DMEM media with 10% FBS over 10 hours or beyond. (FIGS. 2A-2I).

Example 4: General Protocol for Live Cell Reporter Gene Assay

The synthesized pro-coelenterazine or pro-furimazine compounds were evaluated in a live cell reporter gene assay. As shown in FIGS. 3A-C, the luminescent signal decays were monitored over time in HEK293 cells in DMEM media with 10% FBS transfected with 10 ng/well of CMV promoter-NanoLuc® gene with/without adding exogenous esterase porcine liver esterase (PLE) with three representative pro-coelenterazine analogues, e.g. serum instable compound WZ-0308, traditional live cell pro-substrate PBI-4377, and disclosed serum stable compound WZ-0324. The evaluations were performed by the following protocol.

Day 1: Plate cells. HEK293 cells were grown in complete medium (DMEM+10% FBS+1× Non-Essential Amino Acids (NEAA)). The cells were harvested at passasge 6 (~95% confluent), by a procedure of: washing with DPBS, treating the cells with TrypLE Express until cells dislodged, adding 4× volumes of complete medium, pelleting at 188×g for 2 minutes, and suspending the cells in complete medium to 7.35E4 cells/mL. The cells were plated 100 μL per well into the inner 60 wells of 96-well plates (7,350 cells per well): 100 μL DPBS in the 36 outside wells and 100 μL DPBS between wells. The cells were than incubated overnight at 37° C., 5% $CO_2$.

Day 2: Transfection. Two two master mixes (MM) were made: MM#1: 1.63 μL prep #1; 9.5 μL prep #3; 1.9 mL OM1; and MM#2: 2.9 uL prep #2; 9.5 μL prep #3; 1.9 mL OM1. 35.6 μl FuGENE HD was added to each MM and mixed by pipetting up/down. The mixture was incubated for ~10 minutes at room temperature. Next, 8 μL of the mixture was added per well using single channel repeater pipette; n=3 per condition. The mixture was then incubated for ~24 hours at 37° C., 5% $CO_2$.

Day 3: Live cell assay. Stocks of tested compounds in DMSO (500×) were prepared by serial dilution of 50 mM stock with DMSO. The Medium+/− porcine liver esterase (PLE) at room temperature was prepared by adding 1 and 0.333 ug/ml PLE in CO2 IM+10% FBS. CO2 IM+10% FBS with no added PLE was also prepared. Next, medium+test compound solutions (room temperature) was prepared by the steps of: adding 2 mL of respective medium per channel, adding 4 μL respective tested compound stock per channel and mixing by pipetting up/down 10-15×. The final DMSO concentration was 0.2% v/v. The DMSO solution was dropped to the bottom of the channel, showing precipitation for the higher concentrations. After pipetting up/down, solutions with WZ-0324 at a final concentration of ≥50 uM were noticeably hazy (100 uM>75 uM>50 uM), in some cases even after extended incubation at 37° C. The Solutions were allowed to stand at room temperature for 15-20 minutes prior to addition to cells (P1->P2->P3).

The medium was aspirated and replaced with 200 μL/well of respective medium+tested compound solution. DPBS was added to 200 μL total to outside 36× wells. The system was quickly moved to respective GMM+ to start RLU measurements at 37° C. The measuments were carried out under the following conditions: 1 second integration time; RLU measurement every 15 minutes; the lid was removed for the overnight RLU measurements; and initial RLU measurement would be <37° C. owing to the addition of room temperature medium and cooling of the plate.

Data analysis: average RLU plotted for n=3; error represented as standard deviation was included in each imbedded Prism file, but not shown for the sake of clarity in interpreting the curves.

As shown in FIG. 3A, the serum instable compound WZ-0308 in DMEM media containing 10% FBS displayed the highest signal at the initial time point, but rapidly decayed during the first 2-3 hours even without adding exogenous PLE. This result was consistent with the HPLC stability result, indicating WZ-0308 released furimazine rapidly with FBS, but the luminescent signal was not sustainable over a long time. As shown in FIGS. 3B and 3C, both traditional live cell pro-substrate PBI-4377 and disclosed compound WZ-0324 exhibited the stable signal over 24 hours or beyond without adding exogenous PLE esterase. Following the addition of a same amount of PLE esterase, both PBI-4377 and WZ-0324 showed significantly higher luminescence than those without PLE, indicating that they both are PLE substrates and that the luminescent signal can be enhanced immediately by the addition of exogenous esterase. The signal observed for PBI-4377 following PLE addition (FIG. 3B) was generally higher than that of WZ-0324 (FIG. 3C). Without being bound by any theory, it is hypothesized that PBI-4377 might be a better exogenous PLE substrate or a better live cell esterase substrate than the disclosed compound WZ-0324. However, the higher signal of WZ-0324 in the absence of exogenous PLE esterase (FIGS. 3B and 3C) suggested that WZ-0324 might have better cell permeability than PBI-4377. The haze observed at the concentration above 50 μM for PBI-4377 and 70 μM for WZ-324 suggested that WZ-0324 might have an enhanced solubility than PBI-4377.

Compounds WZ-0429, WZ-0439, WZ-0454, WZ-0441, WZ-0451. WZ-0416, WZ-0420, WZ-0461 and WZ-0419 were tested in HEK 293 cells transiently transfected plasmid DNA constructs for SmBiT-PRKACA and LgBiT-PRKAR2A expressed via the HSV-TK promoter in DMEM media with 4% FBS, and the luminescent signal decays were monitored over time. As showed in FIGS. 3I and 3K, the compounds WZ-0451 and WZ-0420 exhibited a stable signal within 15 hours at a concentration above 20 uM, and the strength of signal is 10 times brighter than the traditional pro-substrate PBI-4377 (FIG. 3I and FIG. 3K). However, compounds WZ-0416 and WZ-0461 exhibited a stable signal over 24 hours and beyond in a manner less dependent on the concentration, but with decreased signal strength, which is comparable or slightly better than PBI-4377 (FIGS. 3J, 3K, and FIGS. 4 and 5). In contrast, the serum instable compounds, WZ-0429. WZ-0439, WZ-0454, and WZ-0441 (FIGS. 1A-1H) showed rapid signal decay, almost independent of concentration (FIG. 3A, FIGS. 3E-3H). These results indicate the serum stable compounds, but not serum instable compounds, are capable of tuning reactivity, tuning signal strength, and tuning assay windows, depending on the concentration and the needs of an assay. The evaluations of compounds WZ-0429, WZ-0439, WZ-0454, WZ-0441, WZ-0451. WZ-0416, WZ-0420, WZ-0461 and WZ-0419 were performed by the following protocol.

Day 1, plate cells. HEK293 cells were grow in complete medium [DMEM+10% FBS+1× NEAA]. Cells were plated at approximately 10,000 cells per well (100 µL) in 96-well plates (Corning 3917).

Day 2, transient transfection. Plasmid DNA constructs for SmBiT-PRKACA and LgBiT-PRKAR2A expressed via the HSV-TK promoter were diluted to 6.25 ng/µL in Opti-MEM® I and FuGENE HD was added at a 3:1 lipid:DNA ratio. After a 5-10 minute incubation at room temperature, 8 µl of lipid:DNA solution was added per well, and cells were incubated in a 37° C., 5% CO2 incubator overnight.

Day 3, live cell assay. Compounds were dissolved to 50 mM final in DMSO. Compounds were diluted in DMSO to give 33.3, 16.7 and 6.7 mM stocks. DMSO stock solutions were diluted 667-fold in Opti-MEM® I to give 1× solutions. Complete medium was aspirated and replaced with the respective 1× solution containing 75, 50, 25 or 10 uM of the respective compounds (0.15% v/v DMSO final), such as WZ-0429, WZ-0439, WZ-0454, WZ-0441WZ-0451, WZ-0416, WZ-0420 and WZ-0419, but containing 40, 30, 20 or 10 µM as an instead for compound WZ-0461. Luminescence was measured on a GloMax Multi Plus luminometer every 15 minutes at 37° C. using a 1 second integration time.

Example 5: Complementary Nanoluc Fragment-Fused-Annexin V Binding to Phosphatidylserine for Detecting Apoptosis in Real-Time Format Small and large fragments of luciferase have been engineered as fusion proteins linked to annexin V for detecting of apoptosis in real-time using a plate-reading luminometer. The individual annexin V-luciferase fragment fusion pairs have low intrinsic affinity for each other, and thus produce no or low luminescence in culture medium or in the presence of non-apoptotic cells; but, when the annexin V-luciferase fragment fusion proteins bind in close proximity to phosphatidylserine exposed on the surface of apoptotic cells, the luciferase fragments reconstitute an active enzyme and generate a luminescent signal. The annexin v-luciferase fragment fusion proteins and a luciferase substrate are combined to form a reagent that is added directly to cells in culture to create a homogeneous assay that does not require cell washing steps, which are typically used with fluorescent annexin V binding assays. Monitoring luminescence over time shows the onset of apoptosis precedes secondary necrosis measured from the same sample by multiplexing with a non-permeable fluorogenic DNA binding dye to indicate membrane integrity.

General protocol for complementary NanoLuc® fragment-fused-Annexin V binding: DLD-1 cells (10,000/well; 100 µL) were plated in medium+10% FBS and 2× CellTox Green in a solid white 96-well plate. After the cells were allowed to attach, 50 µL of recombinant human TRAIL at final concentration 500 ng/ml in medium+10% FBS fortified with 1 mM $CaCl_2$ was added. Immediately after, 50 µL of 4× concentrated Annexin-LgBiT and Annexin-SmBiT at final concentration 30 nM and 60 nM were added, and then 50 µL of 4× concentrated test compounds was added at 2-fold serial dilution in medium+10% FBS fortified with 1 mM $CaCl_2$. The plate was incubated at 37° C./5% $CO_2$ in a tissue culture incubator, and luminescence and fluorescence (Ex 485/Em 520) was measured kinetically at the indicated time points. FIGS. 4A-4D show that TRAIL produced dose-dependent increases in luminescence with compound WZ-0336 (t=3.5 hr, 7 hr, 24 hr, and 30 hr, respectively). The kinetically preceded increases in fluorescence of Cytotox Green indicate cell death. This profile indicates the early apoptosis followed by secondary necrosis.

Figure 5A:
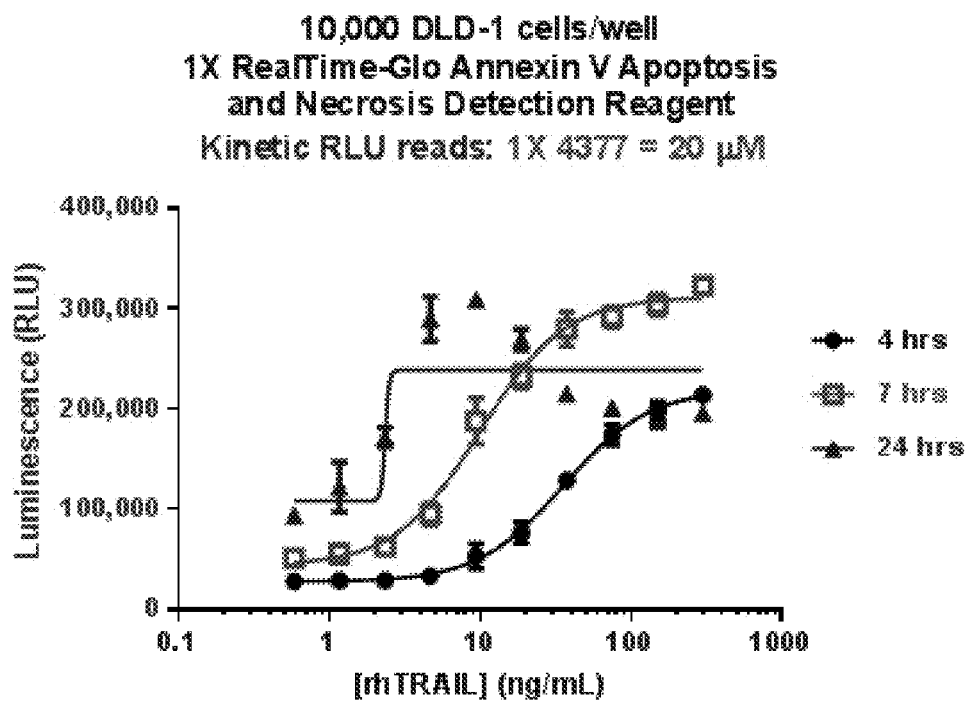
FIGS. 5A-5D show real time Annexin V Apoptosis and necrosis detection in 10,000 DLD-1 cells with dose-dependent rhTRAIL-treatment over 24 hours: PBI-4377 RLU reads (FIG. 5A), PBI-4377 CytotoxGreen RFU reads (FIG. 5B), WZ-0461 RLU reads (FIG. 5C), and WZ-0461 CytotoxGreen RFU reads (FIG. 5D).
Figure 5B:
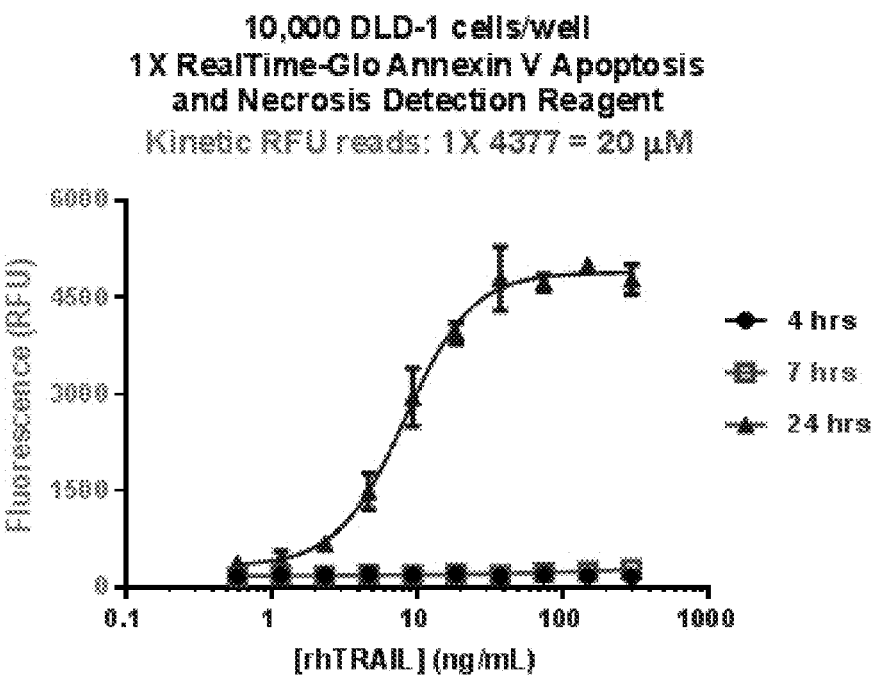
Figure 5C:
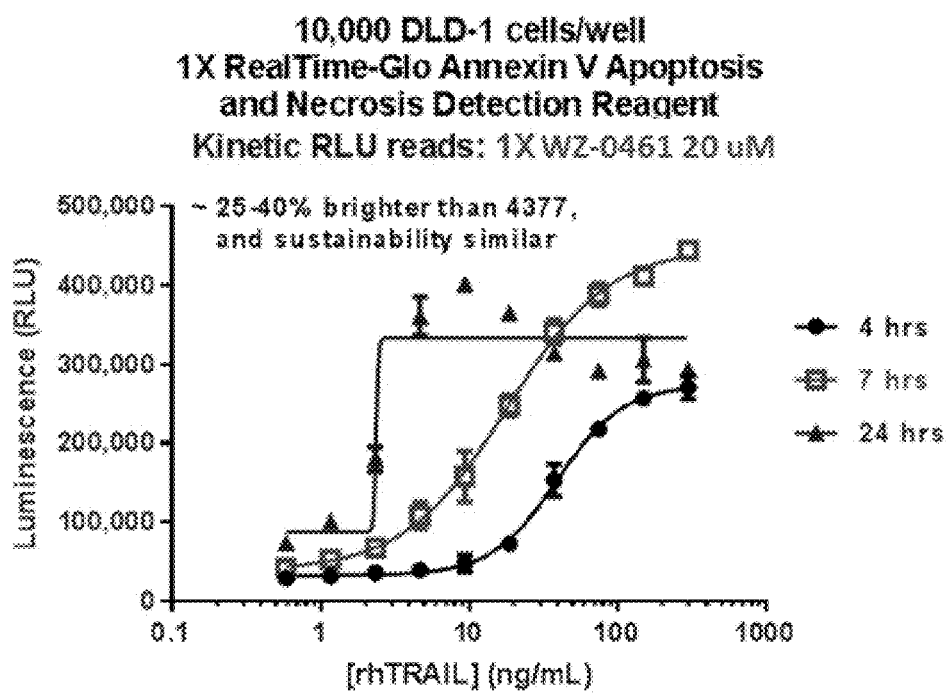
Figure 5D:
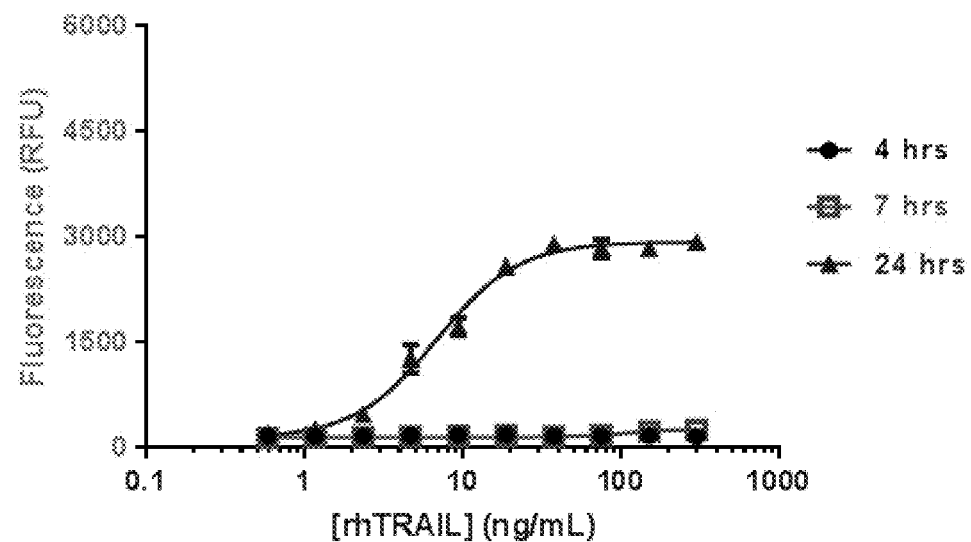

FIGS. 5A-5D show real time Annexin V Apoptosis and necrosis detection in 10,000 DLD-1 cells with dose-dependent rhTRAIL-treament over 24 hours. PBI-4377 RLU reads (FIG. 5A), PBI-4377 CytotoxGreen RFU reads (FIG. 5B); WZ-0461 RLU reads (FIG. 5C), and WZ-0461 CytotoxGreen RFU reads (FIG. 5D)

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A compound of formula (I)

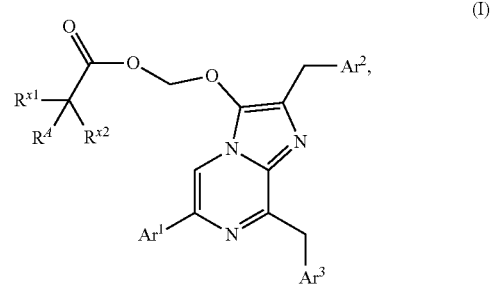

or a tautomer, or a salt thereof, wherein:

$Ar^1$ is phenyl, $Ar^2$ is furyl, and $Ar^3$ is phenyl;

$R^A$ is selected from the group consisting of $C_2$-$C_{10}$ linear or branched alkyl, alkoxy, alkoxyalkyl, amido, acetoxy, methyl ether polyethylene glycoxy, methyl ether polyethylene glycoxyalkyl, haloalkyl, haloalkoxy, aryl, arylalkyl, cycloalkyl, hydroxyl alkyl, hydroxyl polyethylene glycoxyl, carboxyalkyl, heteroaryl, heteroarylalkyl, heterocycle, heterocyclic alkyl, $R^B CH_2$—, $R^C O$—, $R^C C(O)NH$—, and $R^C C(O)O$—, wherein $R^B$ is selected from the group consisting of $C_1$-$C_9$, linear or branched alkyl, alkoxy, alkoxyalkyl, amido, acetoxy, methyl ether polyethylene glycoxy, methyl ether polyethylene glycoxyalkyl, haloalkyl, haloalkoxy, aryl, arylalkyl, cycloalkyl, hydroxyl alkyl, hydroxyl polyethylene glycoxyl, carboxyalkyl, heteroaryl, heteroarylalkyl, heterocycle, and heterocyclic alkyl; and $R^C$ is selected from the group consisting of $C_1$-$C_2$ linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocyclic alkyl;

$R^{x1}$, $R^{x2}$, at each occurrence, are each independently selected from the group consisting of $C_1$-$C_6$ linear or branched alkyl, optionally substituted by one or more substituents selected from the group consisting of alkoxy, aryl, cycloalkyl, heteroaryl, and heterocycle.

2. The compound of claim 1, wherein $R^{x1}$ and $R^{x2}$ are methyl.

3. The compound of claim 1, wherein: $R^A$ is $R^B CH_2$—, wherein $R^B$ is $CH_3(OCH_2CH_2)_nO$—, wherein n is any number from 0-10; or wherein $R^A$ is $R^C O$—, wherein $R^C$ is linear or branched $C_1$—$C_5$—alkyl, or $CH_3(OCH_2CH_2)_n$—, wherein n is any number from 0-10; or wherein $R^A$ is $R^C C(O)NH$—, wherein $R^C$ is linear or branched $C_1$—$C_5$—alkyl; or wherein $R^A$ is $R^C C(O)O$—, wherein $R^C$ is linear or branched $C_1$—$C_5$—alkyl.

4. The compound of claim 1, wherein $R^A$—$C(R^{x1}R^{x2})$— is formula:

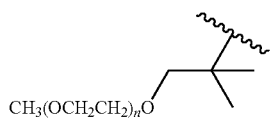

5. The compound of claim 1, wherein the compound of formula (I) has formula (I-d):

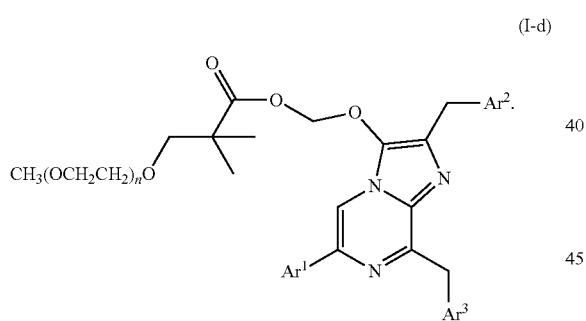

6. The compound of claim 1, wherein the compound of formula (I) has formula (I-e):

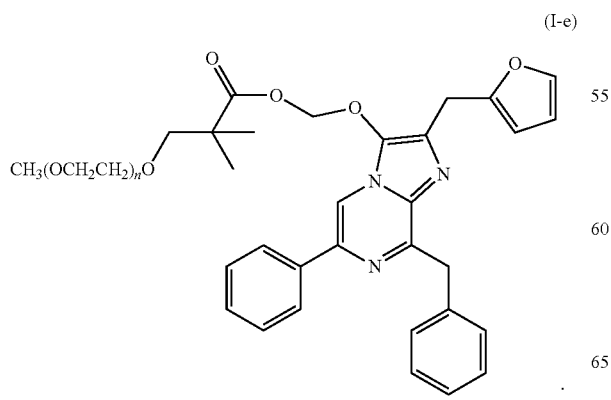

7. The compound of claim 1, wherein $R^A$—$C(R^{x1}R^{x2})$— is formula:

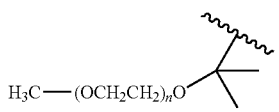

8. The compound of claim 1, wherein the compound of formula (I) has formula (I-f):

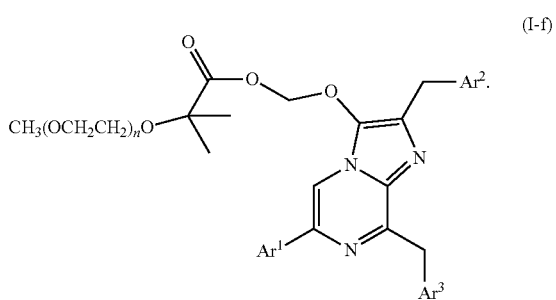

9. The compound of claim 1, wherein the compound of formula (I) has formula (I-g):

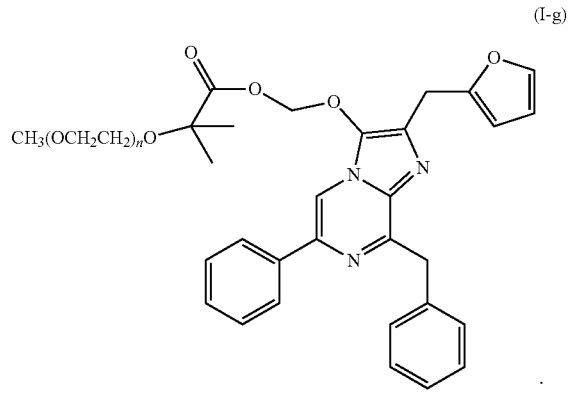

10. The compound of claim 1, wherein the compound of formula (I) has formula (I-h):

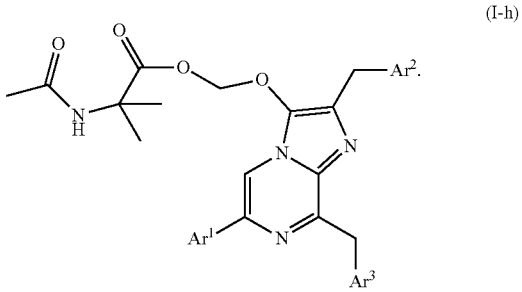

11. The compound of claim 1, wherein the compound of formula (I) has formula (I-j):

(I-j)

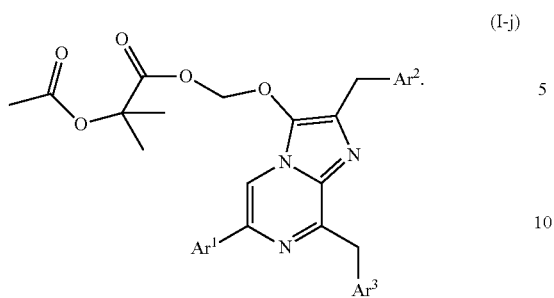

12. The compound of claim 1, wherein the compound of formula (I) has formula (I-k):

(I-k)

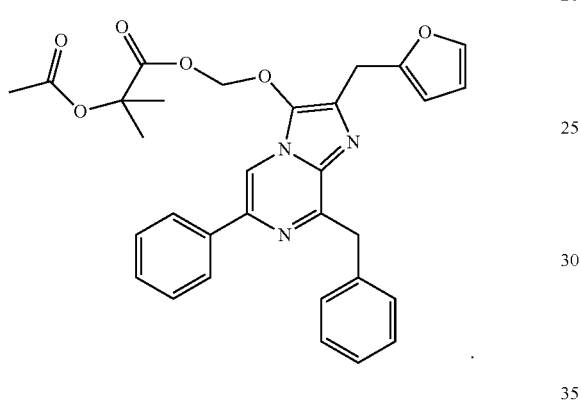

13. A compound of formula (II)

(II)

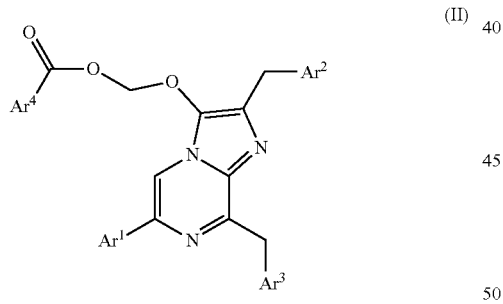

or a tautomer, or a salt thereof, wherein, Ar$^1$, Ar$^2$, and Ar$^3$ are each independently selected from the group consisting of aryl and heteroaryl, wherein Ar$^1$, Ar$^2$, and Ar$^3$ are each optionally substituted; Ar$^4$ is aryl, furan or thiophene, optionally substituted by one or more substituents selected from the group consisting of alkyl, alkoxy, aryl, cycloalkyl, heteroaryl, and heterocycle.

14. The compound of claim 13, wherein Ar$^1$ is phenyl, Ar$^2$ is furyl, and Ar$^3$ is phenyl.

15. The compound of claim 13, Ar$^4$ is phenyl, furan, thiophene, optionally substituted by one or more alkoxy.

16. The compound of claim 13, wherein the compound of formula (II) has formula (II-a), (II-b), or (II-c)

(II-a)

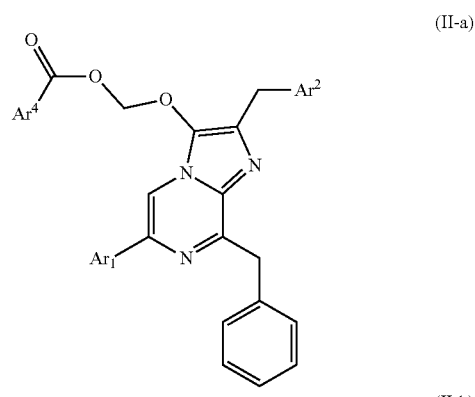

(II-b)

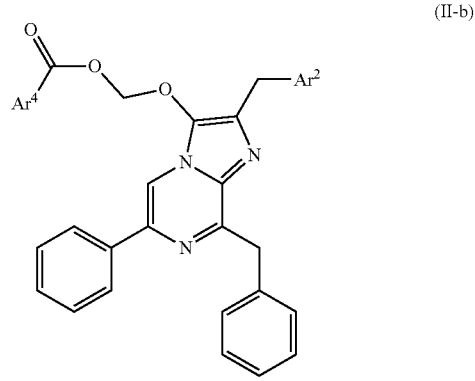

(II-c)

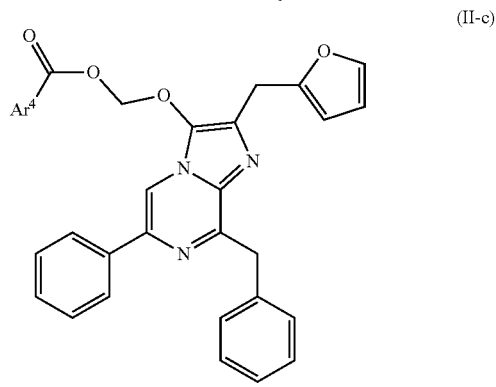

wherein Ar$^1$ is selected from the group consisting of aryl and heteroaryl; Ar$^2$ is selected from the group consisting of aryl and heteroaryl; and Ar$^4$ is phenyl, furan, thiophene, optionally substituted by one or more alkoxy.

17. A compound of formula (III)

(III)

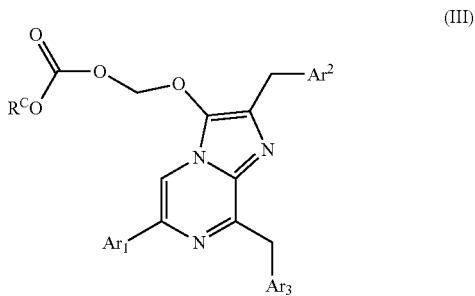

or a tautomer, or a salt thereof, wherein, Ar$^1$, Ar$^2$, and Ar$^3$ are each independently selected from the group consisting of aryl and heteroaryl, wherein $Ar^1$, $Ar^2$, and $Ar^3$ are each optionally substituted; $R^C$ is selected from the group consisting of $C_1$-$C_9$, linear or branched alkyl, alkoxyalkyl, methyl ether poly ethylene glycoxy alkyl, haloalkyl, aryl, arylalkyl, cycloalkyl, hydroxyl alkyl, hydroxyl polyethylene glycoxy alkyl, carboxyalkyl, heteroaryl, heteroarylalkyl, heterocycle, and heterocyclic alkyl.

18. The compound of claim 17, wherein $Ar^1$ is phenyl, $Ar^2$ is furyl, and $Ar^3$ is phenyl.

19. The compound of claim 17, wherein $R^C$ is selected from the group consisting of $C_1$-$C_9$, linear or branched alkyl, alkoxyalkyl, aryl, arylalkyl, cycloalkyl, hydroxyl alkyl, heteroaryl, heteroarylalkyl, heterocycle, and heterocyclic alkyl.

20. The compound of claim 17, wherein the compound of formula (III) has formula (III-a), (III-b), or (III-c)

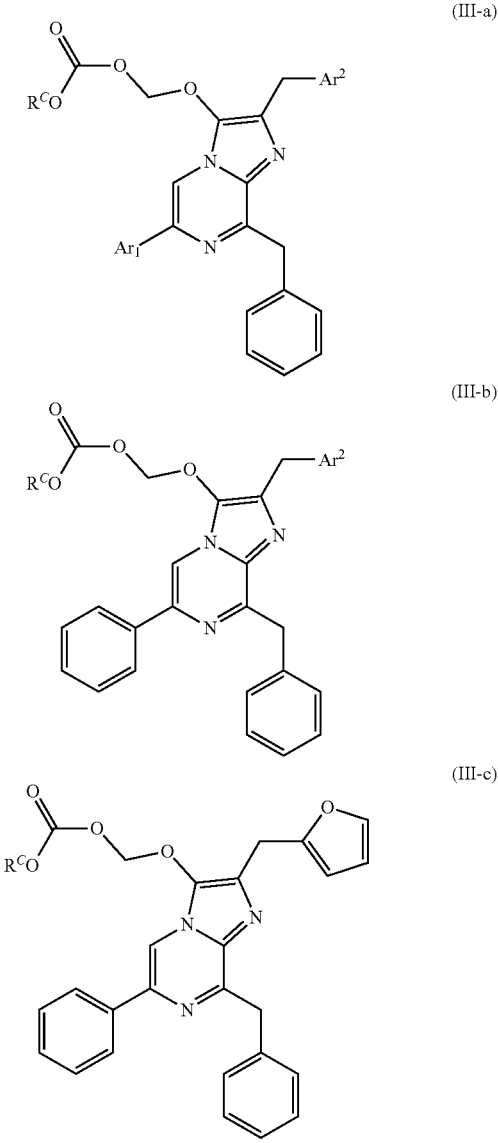

wherein $R^C$ is selected from the group consisting of $C_1$-$C_9$ linear or branched alkyl, alkoxyalkyl, aryl, arylalkyl, cycloalkyl, hydroxyl alkyl, heteroaryl, heteroarylalkyl, heterocycle, and heterocyclic alkyl.

21. The compound of claim 1, selected from the group consisting of:
   ((8-benzyl-2-(furan-2-ylmethyl)-6-phenylimidazo[1,2-a]pyrazin-3-yl)oxy)methyl 3-methoxy-2,2-dimethylpropanoate;
   ((8-benzyl-2-(furan-2-ylmethyl)-6-phenylimidazo[1,2-a]pyrazin-3-yl)oxy)methyl 3-(2-(2-methoxyethoxy)ethoxy)-2,2-dimethylpropanoate;
   ((8-benzyl-2-(furan-2-ylmethyl)-6-phenylimidazo[1,2-a]pyrazin-3-yl)oxy)methyl 3-(2-methoxyethoxy)-2,2-dimethylpropanoate;
   ((8-benzyl-2-(furan-2-ylmethyl)-6-phenylimidazo[1,2-a]pyrazin-3-yl)oxy)methyl 13,13-dimethyl-2,5,8,11-tetraoxatetradecan-14-oate;
   ((8-benzyl-2-(furan-2-ylmethyl)-6-phenylimidazo[1,2-a]pyrazin-3-yl)oxy)methyl 16,16-dimethyl-2,5,8,11,14-pentaoxaheptadecan-17-oate;
   ((8-benzyl-2-(furan-2-ylmethyl)-6-phenylimidazo[1,2-a]pyrazin-3-yl)oxy)methyl 2-methoxy-2-methylpropanoate; and
   ((8-benzyl-2-(furan-2-ylmethyl)-6-phenylimidazo[1,2-a]pyrazin-3-yl)oxy)methyl 2-acetamido-2-methylpropanoate.

22. The compound of claim 13, selected from the group consisting of:
   ((8-benzyl-2-(furan-2-ylmethyl)-6-phenylimidazo[1,2-a]pyrazin-3-yl)oxy)methyl furan-2-carboxylate;
   ((8-benzyl-2-(furan-2-ylmethyl)-6-phenylimidazo[1,2-a]pyrazin-3-yl)oxy)methyl furan-3-carboxylate; and
   ((8-benzyl-2-(furan-2-ylmethyl)-6-phenylimidazo[1,2-a]pyrazin-3-yl)oxy)methyl benzoate.

23. The compound of claim 17, selected from the group consisting of:
   ((8-benzyl-2-(furan-2-ylmethyl)-6-phenylimidazo[1,2-a]pyrazin-3-yl)oxy)methyl methyl carbonate.

24. A kit comprising a compound of claim 1, claim 13, or claim 17.

25. The kit of claim 24, further comprising a deprotection enzyme, wherein the deprotection enzyme is an esterase.

26. The kit of claim 24, further comprising a luciferase or a fragment complementary luciferase.

27. The kit of claim 24, further comprising a buffer reagent.

28. A method for detecting luminescence in a sample, the method comprising: contacting a sample with a compound of claim 1, claim 13, or claim 17; contacting the sample with an esterase, if no esterase is present in the sample; contacting the sample with a coelenterazine-utilizing luciferase, if no coelenterazine-utilizing luciferase is present in the sample; and detecting luminescence.

29. The method of claim 28, wherein the sample comprises live cells.

30. The method of claim 28, wherein the sample comprises a coelenterazine-utilizing luciferase or a fragment complementary luciferase.

31. A method for detecting luminescence in a transgenic animal comprising administering a compound of claim 1, claim 13, or claim 17 to a transgenic animal; and
   detecting luminescence; wherein the transgenic animal expresses a coelenterazine-utilizing luciferase.

* * * * *

UNITED STATES PATENT AND TRADEMARK OFFICE
CERTIFICATE OF CORRECTION

PATENT NO. : 10,836,767 B2
APPLICATION NO. : 16/023950
DATED : November 17, 2020
INVENTOR(S) : Wenhui Zhou et al.

It is certified that error appears in the above-identified patent and that said Letters Patent is hereby corrected as shown below:

Claim 1, Column 51, Line 5 reads:
"$C_1$-$C_2$ linear or branched alkyl, alkoxyalkyl, methyl"
Whereas it should read:
"$C_1$-$C_9$ linear or branched alkyl, alkoxyalkyl, methyl"

Claim 19, Column 55, Line 12 reads:
"from the group consisting of $C_1$-$C_9$, linear or branched alkyl,"
Whereas it should read:
"from the group consisting of $C_1$-$C_9$ linear or branched alkyl,"

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*